(12) United States Patent
Sato

(10) Patent No.: US 10,993,698 B2
(45) Date of Patent: May 4, 2021

(54) ULTRASONIC DIAGNOSTIC APPARATUS AND SIGNAL PROCESSING APPARATUS

(71) Applicant: Toshiba Medical Systems Corporation, Otawara (JP)

(72) Inventor: Takeshi Sato, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 423 days.

(21) Appl. No.: 15/254,303

(22) Filed: Sep. 1, 2016

(65) Prior Publication Data

US 2017/0071575 A1   Mar. 16, 2017

(30) Foreign Application Priority Data

Sep. 14, 2015   (JP) .............................. JP2015-181126

(51) Int. Cl.
| | |
|---|---|
| *A61B 8/08* | (2006.01) |
| *A61B 8/00* | (2006.01) |
| *A61B 8/06* | (2006.01) |
| *G01S 15/89* | (2006.01) |
| *G01S 7/52* | (2006.01) |

(52) U.S. Cl.
CPC .............. *A61B 8/5207* (2013.01); *A61B 8/06* (2013.01); *A61B 8/4488* (2013.01); *A61B 8/5223* (2013.01); *A61B 8/5276* (2013.01); *A61B 8/54* (2013.01); *G01S 7/52038* (2013.01); *G01S 15/8981* (2013.01)

(58) Field of Classification Search
None
See application file for complete search history.

(56) References Cited

U.S. PATENT DOCUMENTS

| | | | |
|---|---|---|---|
| 6,267,725 B1 * | 7/2001 | Dubberstein ....... | G01S 7/52033 600/443 |
| 8,568,319 B1 * | 10/2013 | Kaplan ................ | A61B 8/56 600/437 |
| 2007/0167752 A1 * | 7/2007 | Proulx ............... | G01S 7/52095 600/437 |

(Continued)

FOREIGN PATENT DOCUMENTS

| | | |
|---|---|---|
| JP | H11-056846 A | 3/1999 |
| JP | 3724846 | 12/2005 |

(Continued)

OTHER PUBLICATIONS

Japanese Office Action dated Mar. 5, 2019, issued in Japanese Patent Application No. 2015-181126.

(Continued)

*Primary Examiner* — Jonathan Cwern

(74) *Attorney, Agent, or Firm* — Oblon, McClelland, Maier & Neustadt, L.L.P.

(57) ABSTRACT

An ultrasonic diagnostic apparatus according to an embodiment includes filter processing circuitry and generation circuitry. The filter processing circuitry performs a filter process of removing a still or minute-moving signal on reflected wave signals of an ultrasonic wave transmitted a plurality of times in the same scanning line. The generation circuitry generates reflected wave data through a phasing addition process using reflected wave signal of each channel after the filter process performed by the filter processing circuitry.

5 Claims, 17 Drawing Sheets

(56) References Cited

U.S. PATENT DOCUMENTS

| | | | |
|---|---|---|---|
| 2007/0282203 A1* | 12/2007 | Baba | A61B 8/488 600/453 |
| 2007/0288178 A1* | 12/2007 | Bonnefous | F15B 7/06 702/48 |
| 2014/0039317 A1* | 2/2014 | Sato | A61B 8/54 600/443 |
| 2014/0121519 A1 | 5/2014 | Miyajima et al. | |
| 2014/0369624 A1 | 12/2014 | Ward | |
| 2015/0366541 A1 | 12/2015 | Okumura et al. | |

FOREIGN PATENT DOCUMENTS

| | | |
|---|---|---|
| JP | 2011-172933 A | 9/2011 |
| JP | 2013-352 | 1/2013 |
| JP | 2013-31654 | 2/2013 |
| JP | 2013-063159 A | 4/2013 |
| JP | 2014-42823 | 3/2014 |
| JP | 2014-158598 A | 9/2014 |
| JP | 2014-176607 | 9/2014 |
| JP | 2015-2557 | 1/2015 |

OTHER PUBLICATIONS

U.S. Appl. No. 14/039,972, filed Sep. 27, 2013, 2014/0039317 A1, Takeshi Sato.
U.S. Appl. No. 14/803,726, filed Jul. 20, 2015, 2015/0320395 A1, Takeshi Sato.

\* cited by examiner

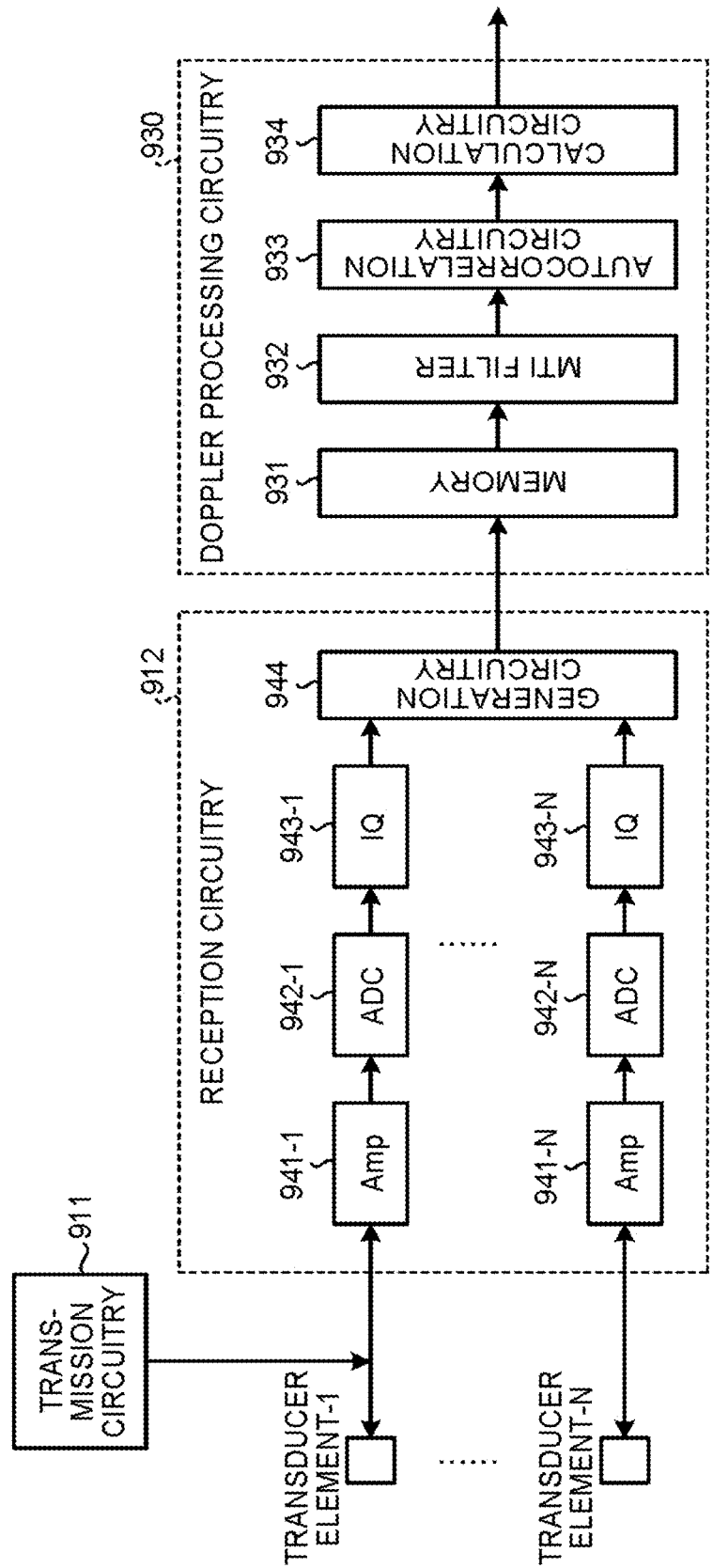

i-TH SAMPLE POINT IN DEPTH DIRECTION
RECEPTION SIGNAL x(i,1)

i-TH SAMPLE POINT IN DEPTH DIRECTION
RECEPTION SIGNAL x(i,2)

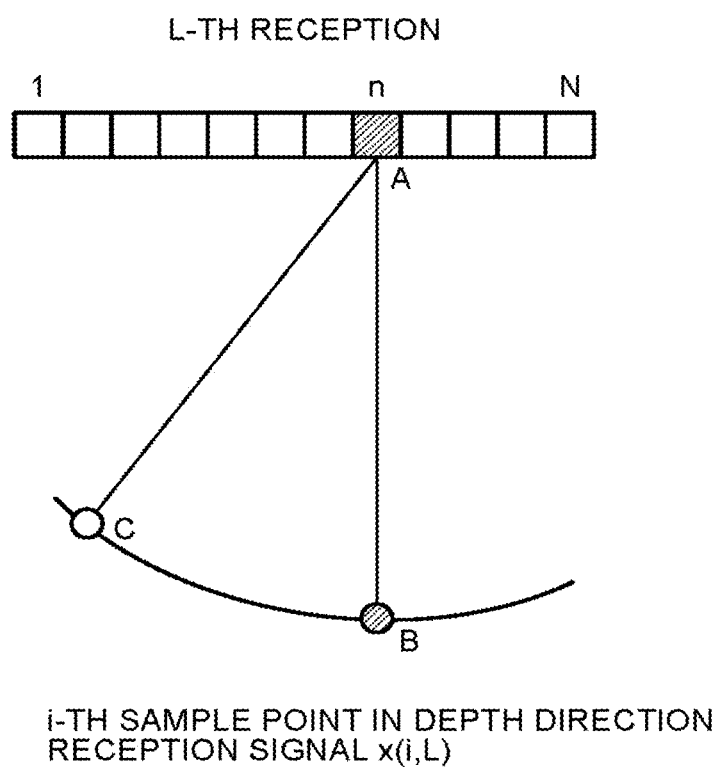

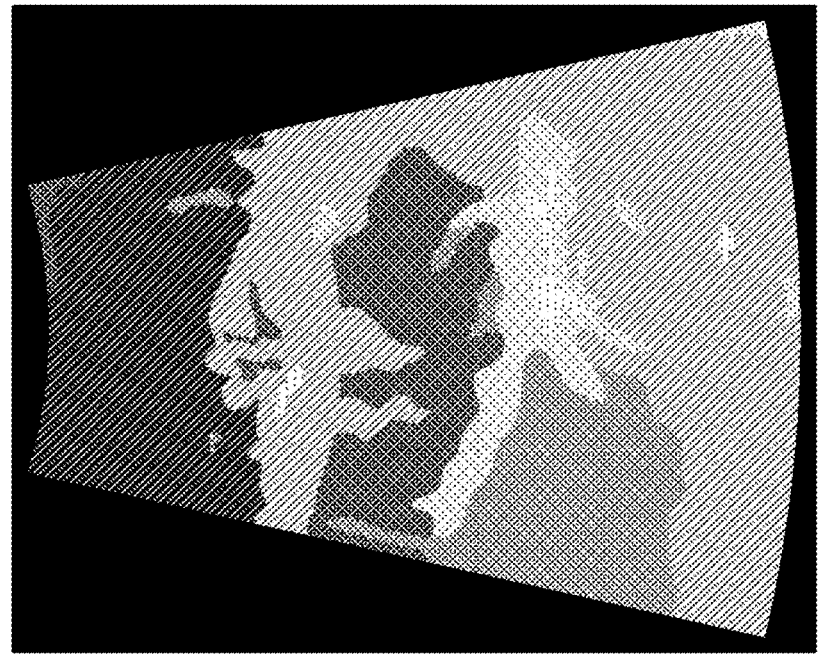
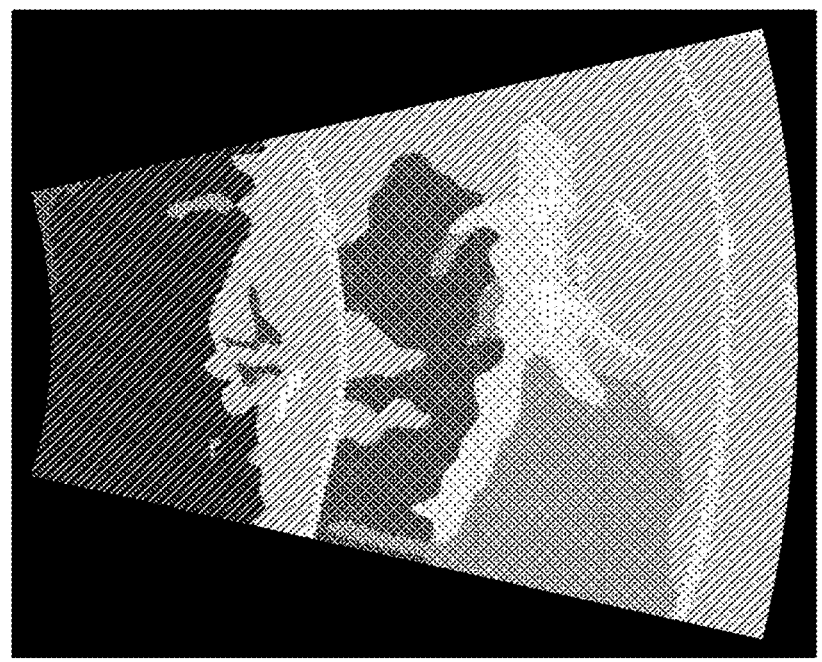
FIG.10

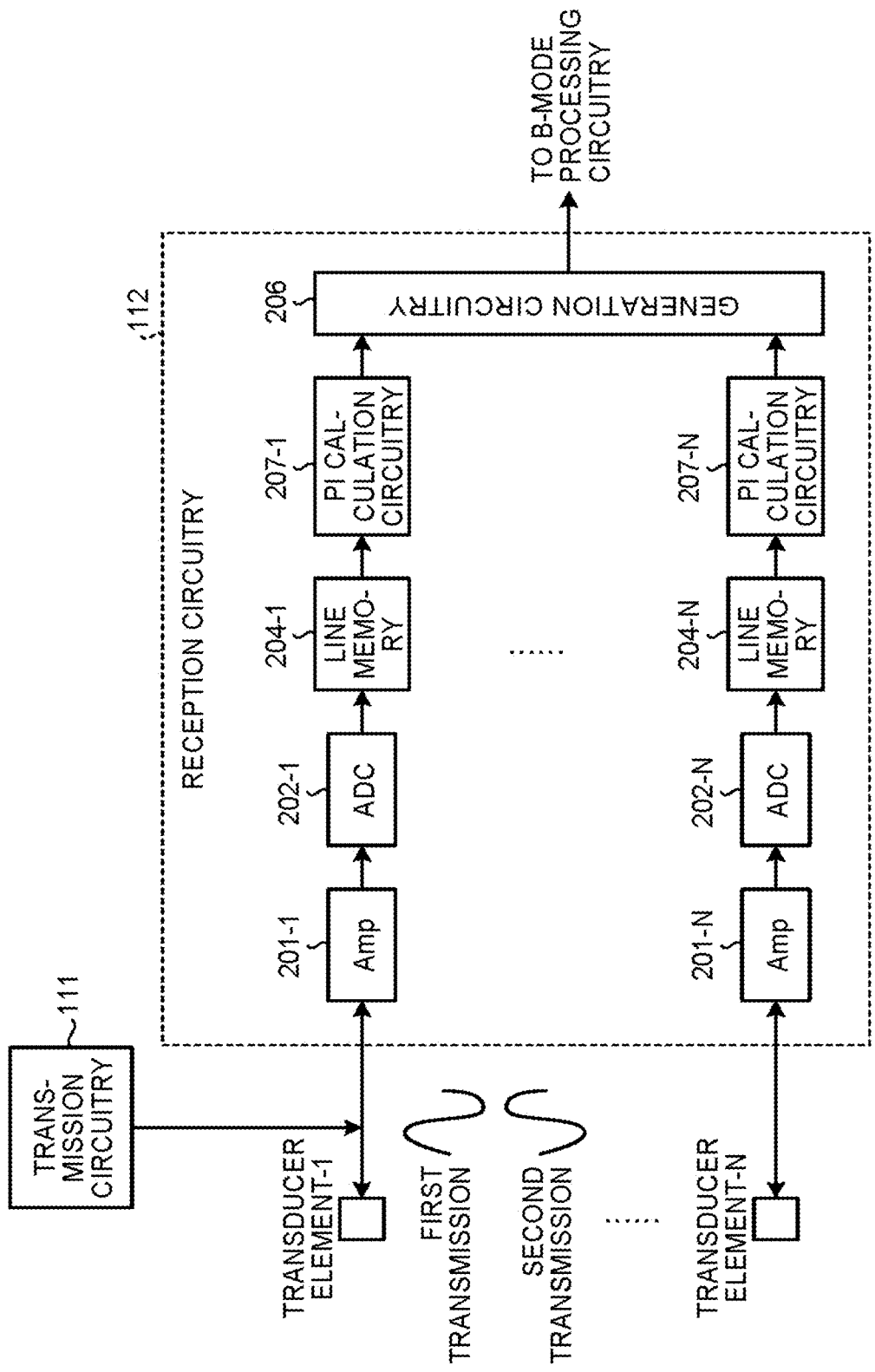

ULTRASONIC DIAGNOSTIC APPARATUS AND SIGNAL PROCESSING APPARATUS

CROSS-REFERENCE TO RELATED APPLICATIONS

This application is based upon and claims the benefit of priority from Japanese Patent Application No. 2015-181126, filed on Sep. 14, 2015; the entire contents of which are incorporated herein by reference.

FIELD

Embodiments described herein relate generally to an ultrasonic diagnostic apparatus and a signal processing apparatus.

BACKGROUND

In recent years, by performing plane wave transmission or transmission covering a wide range similar to the plane wave transmission, all received rasters within an ultrasonic wave frame can be acquired in real time at one-time transmission. Herein, this will be referred to as all-raster parallel simultaneous reception. By applying the all-raster parallel simultaneous reception to a blood flow imaging method using data between frames, a blood flow display system capable of detecting a low speed to a high speed in high frame rate display can be built. Since a transmission interval for a blood flow and a frame period match each other, high frame rate display and a high instant speed are secured, and an observation time of infinity can be acquired. Accordingly, a steep moving target indicator (MTI) filter having a low cutoff frequency can be configured, and detection can be performed up to a low-speed blood flow while suppressing low-speed clutter.

BRIEF DESCRIPTION OF THE DRAWINGS

FIG. 7 is a diagram that illustrates an example of the configuration of reception circuitry and Doppler processing circuitry according to the conventional technology;

FIG. 9C is a diagram that illustrates the first embodiment;

FIG. 10 is a diagram that illustrates an effect of an ultrasonic diagnostic apparatus according to the first embodiment;

FIG. 12 is a block diagram that illustrates an example of the configuration of reception circuitry according to a third embodiment.

DETAILED DESCRIPTION

Hereinafter, ultrasonic diagnostic apparatuses and signal processing apparatuses according to embodiments will be described with reference to the drawings. However, the embodiments are not limited to the following embodiments. In principle, a content described in one embodiment is similarly applied to the other embodiments.

An ultrasonic diagnostic apparatus according to an embodiment includes filter processing circuitry and generation circuitry. The filter processing circuitry performs a filter process of removing a still or minute-moving signal on reflected wave signals of an ultrasonic wave transmitted a plurality of times in the same scanning line. The generation circuitry generates reflected wave data through a phasing addition process using reflected wave signal of each channel after the filter process performed by the filter processing circuitry.

First Embodiment

Figure 1:
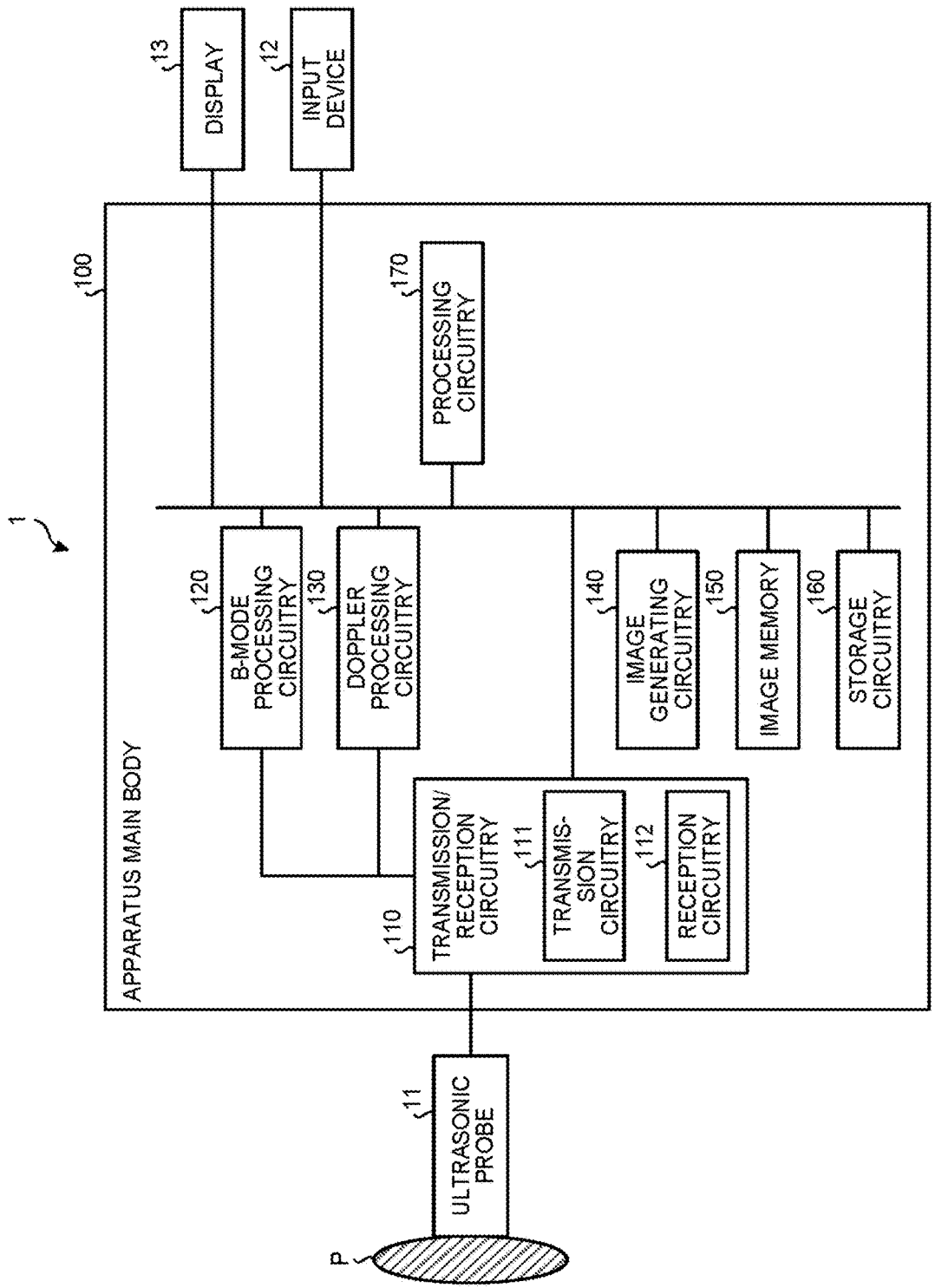
FIG. 1 is a block diagram that illustrates an example of the configuration of an ultrasonic diagnostic apparatus according to a first embodiment.

FIG. 1 is a block diagram that illustrates an example of the configuration of an ultrasonic diagnostic apparatus 1 according to a first embodiment. As illustrated in FIG. 1, the ultrasonic diagnostic apparatus 1 according to the first embodiment includes: an ultrasonic probe 11; an input device 12; a display 13; and an apparatus main body 100. The ultrasonic probe 11 is communicably connected to transmission/reception circuitry 110 included in the apparatus main body 100 to be described later. In addition, the input device 12 and the display 13 are communicably connected to various circuitry included in the apparatus main body 100.

The ultrasonic probe 11 is brought into contact with a body surface of a subject P and transmits and receives ultrasonic waves. For example, the ultrasonic probe 11 includes a plurality of piezoelectric transducer elements (also referred to as transducer elements). The plurality of piezoelectric transducer elements generate ultrasonic waves based on a transmission signal supplied from the transmission/reception circuitry 110. The generated ultrasonic waves are reflected on an in-body tissue of the subject P and are received by the plurality of piezoelectric transducer elements as reflected wave signals. The ultrasonic probe 11 transmits the reflected wave signals received by the plurality of piezoelectric transducer elements to the transmission/reception circuitry 110.

In the first embodiment, the ultrasonic probe 11 may be applied as a 1D array probe that scans a two-dimensional area inside a subject P (two-dimension scanning) or a mechanical 4D probe or a 2D array probe that scans a three-dimensional area inside a subject P (three-dimensional scanning).

The input device 12, for example, corresponds to a mouse, a keyboard, a button, a panel switch, a touch command screen, a foot switch, a trackball, a joystick, or the like. The input device 12 receives various setting requests from an operator of the ultrasonic diagnostic apparatus 1 and appropriately transmits the received various setting requests to circuitry of the apparatus main body 100.

The display 13 displays a graphical user interface (GUI) used for operator's inputting various setting requests using the input device 12 or displays an image (ultrasonic wave image) based on ultrasonic wave image data generated by the apparatus main body 100 or the like.

The apparatus main body 100 is a device that generates ultrasonic wave image data based on reflected wave signals received by the ultrasonic probe 11. As illustrated in FIG. 1, the apparatus main body 100, for example, includes: transmission/reception circuitry 110; B-mode processing circuitry 120; Doppler processing circuitry 130; image generating circuitry 140; an image memory 150; storage circuitry 160; and processing circuitry 170. The transmission/reception circuitry 110, the B-mode processing circuitry 120, the Doppler processing circuitry 130, the image generating circuitry 140, the image memory 150, the storage circuitry 160; and the processing circuitry 170 are connected to be communicable with each other.

The transmission/reception circuitry 110 controls the transmission/reception of ultrasonic waves using the ultrasonic probe 11. For example, the transmission/reception circuitry 110 includes transmission circuitry 111 and reception circuitry 112 and controls the transmission/reception of ultrasonic waves performed by the ultrasonic probe 11 based on an instruction from the processing circuitry 170 to be described later. The transmission circuitry 111 generates transmission waveform data and generates a transmission signal used for the ultrasonic probe 11 to transmit an ultrasonic wave based on the generated transmission waveform data. Then, the transmission circuitry 111 applies the transmission signal to the ultrasonic probe 11, thereby transmitting an ultrasonic beam in which the ultrasonic wave converges in a beam shape.

For example, the transmission circuitry 111 causes the ultrasonic probe 11 to perform ultrasonic wave scanning transmitting a plane wave under the control of the processing circuitry 170. In addition, the transmission circuitry 111 causes the ultrasonic probe 11 to perform ultrasonic wave scanning receiving reflected wave signals in a plurality of scanning lines.

In addition, the transmission circuitry 111 causes the ultrasonic probe 11 to perform ultrasonic wave scanning using a data row between frames as a Doppler data row under the control of the processing circuitry 170 (see Japanese Patent No. 3724846 and Japanese Patent Application Publication No. 2014-42823). For example, the transmission circuitry 111 causes the ultrasonic probe 11 to perform first ultrasonic wave scanning acquiring information relating to a motion of a moving body within a first scanning range and causes the ultrasonic probe 11 to perform ultrasonic wave scanning of each of a plurality of divided ranges acquired by dividing a second scanning range as second ultrasonic wave scanning acquiring information of a shape of a tissue within the second scanning range in a time divisional manner during the first ultrasonic wave scanning under the control of the processing circuitry 170.

Furthermore, the transmission circuitry 111 causes the ultrasonic probe 11 to perform ultrasonic wave scanning having a first transmission ultrasonic wave and a second transmission ultrasonic wave acquired by inverting the phase of the first transmission ultrasonic wave as one set under the control of the processing circuitry 170.

The reception circuitry 112 generates reflected wave data in which a reflection component reflected from a direction corresponding to the reception directivity of a reflected wave signal is emphasized by performing an addition process with a predetermined delay time applied to the reflected wave signal received by the ultrasonic probe 11 and transmits the generated reflected wave data to the B-mode processing circuitry 120 and the Doppler processing circuitry 130.

For example, the reception circuitry 112 includes: amplification circuitry (described as an "Amp" as is appropriate); an analog/digital (A/D) converter (described as an "ADC" as is appropriate); generation circuitry; quadrature detection circuitry (described as an "IQ" as is appropriate); and the like. The amplification circuitry performs a gain correction process by amplifying a reflected wave signal for each channel. The A/D converter performs A/D conversion of the gain-corrected reflected wave signals.

The generation circuitry applies a reception delay time that is necessary for determining the reception directivity to digital data. Then, the generation circuitry performs an addition process of adding the reflected wave signals for which the reception delay time has been applied. According to the addition process performed by the generation circuitry, reflection components, which are reflected from a direction corresponding to the reception directivity, of the reflected wave signals are emphasized.

Then, the quadrature detection circuitry converts an output signal of the adder into an in-phase signal (I signal, I: in-phase) and a quadrature signal (Q signal, Q: quadrature phase) of a baseband. Then, the quadrature detection circuitry stores the I signal and the Q signal (hereinafter, referred to as IQ signals) in a buffer as reflected wave data. In addition, the quadrature detection circuitry may convert the output signal of the adder into a radio frequency (RF) signal and then store the RF signal stored in a buffer. The IQ signals and the RF signal are signals (reception signals) in which phase information is included. While the quadrature detection circuitry has been described to be arranged on a rear stage of the generation circuitry, the embodiment is not limited thereto. For example, the quadrature detection circuitry may be arranged on a front stage of the generation circuitry. In such a case, the generation circuitry performs an addition process of adding an I signal and a Q signal.

The B-mode processing circuitry 120 performs various kinds of signal processing for the reflected wave data generated based on the reflected wave signals by the reception circuitry 112. The B-mode processing circuitry 120 performs logarithmic amplification, an envelope detection process, and the like for the reflected wave data received from the reception circuitry 112 and generates data (B mode data) in which a signal intensity for each sample point (observation point) is represented as the brightness of luminance. The B-mode processing circuitry 120 transmits the generated B mode data to the image generating circuitry 140.

In addition, the B-mode processing circuitry 120 performs signal processing used for performing harmonic imaging that images harmonic components. As the harmonic imaging, contrast harmonic imaging (CHI) and tissue harmonic imaging (THI) are known. In addition, in the contrast harmonic imaging or the tissue harmonic imaging, as a scanning system, amplitude modulation (AM), phase modulation (PM) called a "pulse subtraction method" or a "pulse inversion method", and AMPM capable of acquiring both the effects of the AM and the effects of the PM by combining the AM and the PM are known.

The Doppler processing circuitry 130 generates data (Doppler data) acquired by extracting motion information based on the Doppler effect of a moving body from the reflected wave data received from the reception circuitry 112 as sample points within the scanning area. More specifically, the Doppler processing circuitry 130 generates Doppler data acquired by extracting an average speed, a variance value, a power value, and the like as motion information of the moving body as sample points. Herein, the moving body, for example, is a blood flow, a tissue such as a cardiac wall, or an imaging agent. The Doppler processing circuitry 130 transmits the generated Doppler data to the image generating circuitry 140.

The image generating circuitry 140 generates ultrasonic wave image data based on the data generated by the B-mode processing circuitry 120 and the Doppler processing circuitry 130. For example, the image generating circuitry 140 generates B-mode image data representing the intensity of a reflected wave as luminance based on the B mode data generated by the B-mode processing circuitry 120. In addition, the image generating circuitry 140 generates Doppler image data representing moving body information based on the Doppler data generated by the Doppler processing circuitry 130. This Doppler image data is speed image data, variance image data, power image data, or image data combining these.

The image memory 150 is a memory that stores data generated by the B-mode processing circuitry 120, the Doppler processing circuitry 130, and the image generating circuitry 140. For example, the image memory 150 stores the ultrasonic wave image data generated by the image generating circuitry 140 in association with an electrocardiographic waveform of a subject P. In a case where the amount of data stored in the image memory 150 exceeds the storage capacity of the image memory 150, data is erased in order of old data to new data, and the image memory is updated.

The storage circuitry 160 is a storage device that stores various kinds of data. For example, the storage circuitry 160 stores control programs used for the transmission/reception of ultrasonic waves, image processing, and a display process, diagnosis information (for example, a patient ID, a doctor's opinion, or the like), and various kinds of data such as a diagnosis protocol and various kinds of body marks. In addition, the data stored in the storage circuitry 160 may be transmitted to an external device through an interface unit not illustrated in the drawing.

In addition, the storage circuitry 160 stores data stored by the B-mode processing circuitry 120, the Doppler processing circuitry 130, and the image generating circuitry 140. For example, the storage circuitry 160 stores ultrasonic wave image data corresponding to a predetermined heart rate designated by an operator. In addition, the storage circuitry 160 is an example of a storage unit that stores a plurality of images acquired by scanning a subject P for a predetermined period.

The processing circuitry 170 controls the whole process of the ultrasonic diagnostic apparatus 1. More specifically, the processing circuitry 170 controls the processes of the transmission/reception circuitry 110, the B-mode processing circuitry 120, the Doppler processing circuitry 130, the image generating circuitry 140, and the like based on various kinds of setting requests input from an operator through the input device 12 and various kinds of control programs and various kinds of data read from the storage circuitry 160. In addition, the processing circuitry 170 displays the ultrasonic wave image data stored in the image memory 150 on the display 13.

For example, the processing circuitry 170 causes the ultrasonic probe 11 to perform ultrasonic wave scanning transmitting a plane wave by controlling the transmission circuitry 111. In addition, for example, the processing circuitry 170 causes the ultrasonic probe 11 to perform ultrasonic wave scanning receiving reflected wave signals in a plurality of scanning lines by controlling the transmission circuitry 111. Furthermore, for example, the processing circuitry 170, by controlling the transmission circuitry 111, causes the ultrasonic probe 11 to perform first ultrasonic wave scanning acquiring information relating to a motion of a moving body within a first scanning range and causes the ultrasonic probe 11 to perform ultrasonic wave scanning of each of a plurality of divided ranges acquired by dividing a second scanning range during the first ultrasonic wave scanning in a time divisional manner as second ultrasonic wave scanning acquiring information of a shape of a tissue within the second scanning range. In addition, for example, the processing circuitry 170, by controlling the transmission circuitry 111, causes the ultrasonic probe 11 to perform ultrasonic wave scanning having a first transmission ultrasonic wave and a second transmission ultrasonic wave acquired by inverting the phase of the first transmission ultrasonic wave as one set.

A plurality of constituent elements illustrated in FIG. 1 may be integrated into one processor so as to realize the functions thereof. The term "processor" used in the above description, for example, represents a central processing unit (CPU), a graphics processing unit (GPU), or a circuitry such as an application specific integrated circuit (ASIC), a programmable logic device (for example, a simple programmable logic device (SPLD), a complex programmable logic device (CPLD), and a field programmable gate array (FPGA)), or the like. The function of the processor is realized by reading and executing a program stored in the storage circuitry 160. Instead of storing the program in the storage circuitry 160, the program may be directly built in a circuitry of the processor. In such a case, as the processor reads and executes the program built in the circuitry of the processor, the function thereof is realized. Each processor according to this embodiment is not limited to being configured as a single circuit for each processor, but the function thereof may be realized by configuring one processor by combining a plurality of independent circuits.

In the ultrasonic diagnostic apparatus 1 configured in this way, a method (color Doppler method) imaging a blood flow by using an ultrasonic wave has been widely and generally used. However, in a case where the level of a minute blood flow signal according to a scattering echo from a red blood cell is set to 0 dB, a specular reflection echo from a vessel wall or a diaphragm is 100 dB or more. The value of a reflected wave signal of a strong reflector such as the vessel wall or the diaphragm exceeds far beyond the limit (generally, about 60 dB) of the dynamic range of a reflected wave signal from one element of the ultrasonic diagnostic apparatus 1. For this reason, a reflected wave signal from the vessel wall or the diaphragm is saturated mainly by amplification circuitry of the reception circuitry 112. In a color Doppler mode, in order to acquire a minute blood flow signal having a good S/N ratio, in a normal reception condition, the gain of the amplification circuitry is set to be high. For this reason, a reflected wave signal from a strong reflector is saturated. If a signal of a channel CH (one reception circuitry exists so as to correspond to one transducer element of a probe and one block is referred to as a channel (CH)) is saturated, a main lobe is decreased, and a side lobe is increased.

Figure 2:
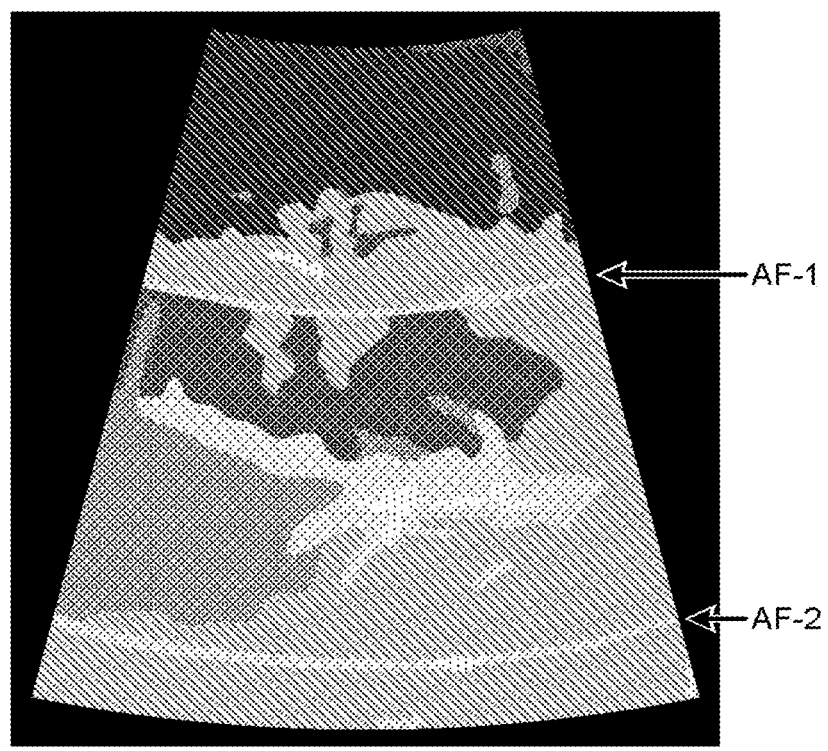
FIG. 2 is a diagram that illustrates an example of a case where blood flow information is power-displayed.

In addition, in recent years, a method of acquiring an ultra-high frame rate by receiving all rasters at one-time transmission has been put into practical use. In such a case, although plane wave transmission is performed without applying transmission focusing, if the blood flow is imaged by such a method, there are cases where arc-shaped artifacts occur as illustrated in FIG. 2. FIG. 2 is a diagram that illustrates an example of a case where blood flow information is power-displayed. In FIG. 2, an example of a case where blood flow information is power-displayed is illustrated. In FIG. 2, the cases where artifacts AF-1 and AF-2 occur are illustrated. This is because some channel CH is saturated by an echo from a strong reflector, so that the side lobe is increased, and the strong reflector is moved so that a signal passes through the MTI filter and a side lobe region of the strong reflector is displayed like a blood flow signal. Since the saturation occurs before beam forming, by observing reflected wave data after the beam forming, it cannot be recognized whether or not the saturation is formed.

Figure 3:
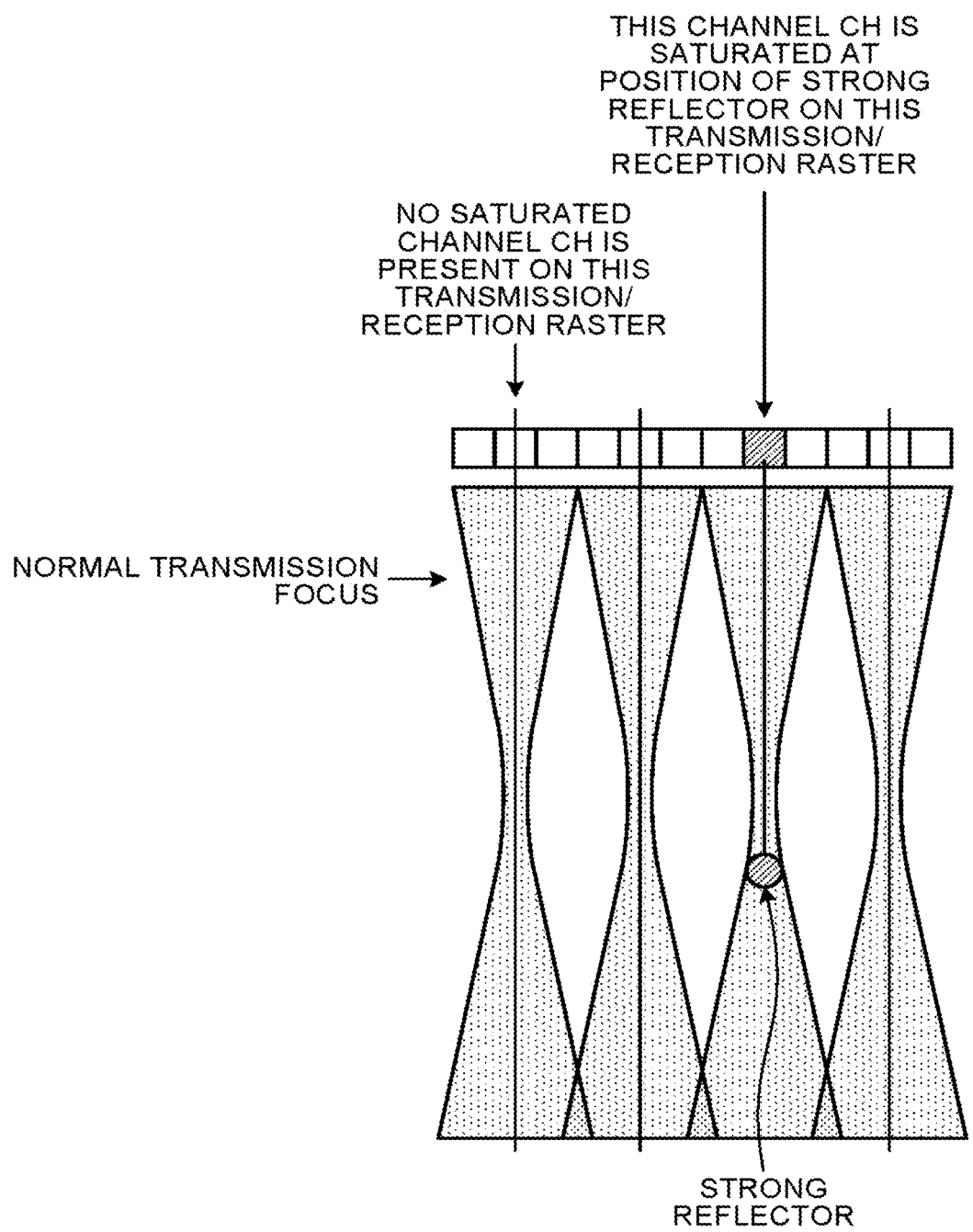
FIG. 3 is a diagram that illustrates an example of a sound field in general ultrasonic wave transmission.

In case of the plane wave transmission+all-raster parallel simultaneous reception, a reason for the occurrence of arc-shaped artifacts as illustrated in FIG. 2 will be described. FIG. 3 is a diagram that illustrates an example of a sound field in general ultrasonic wave transmission, and FIG. 4 is a diagram that illustrates an example of a sound field in plane wave transmission.

In the general ultrasonic wave transmission illustrated in FIG. 3, transmission focusing is applied on a raster same as a reception raster of an ultrasonic wave, and one raster is received for one-time transmission. In other words, since focusing is applied for both transmission and reception, a side lobe level of the transmission/reception sound field is low, and only reflected waves of a reflector that is present approximately on the raster are received. In a typical color Doppler method, since a blood flow sensitivity takes precedence, it cannot be avoided that the reflected wave signal is saturated by the strong reflector. For example, there is a case where a side lobe of the gallbladder wall inside the gallbladder is displayed like a blood flow. This is because the level of the side lobe is increased by saturation and the gallbladder wall is moved. In addition, in the case where one raster is received for one-time transmission, even in a case where a reflected wave signal of a specific channel (CH) is saturated by a reflected wave signal from a strong reflector, the influence of the saturation is limited only to the place thereof. In such a case, even when a blood flow signal is erroneously recognized and displayed, it is well known that a strong reflector is incorrectly displayed as a blood flow signal, and thus, there is no serious problem. In addition, the speed may be calculated, and, based on a logic not displaying a signal in case of a low speed, the strong reflector may be configured not be displayed.

Figure 4:
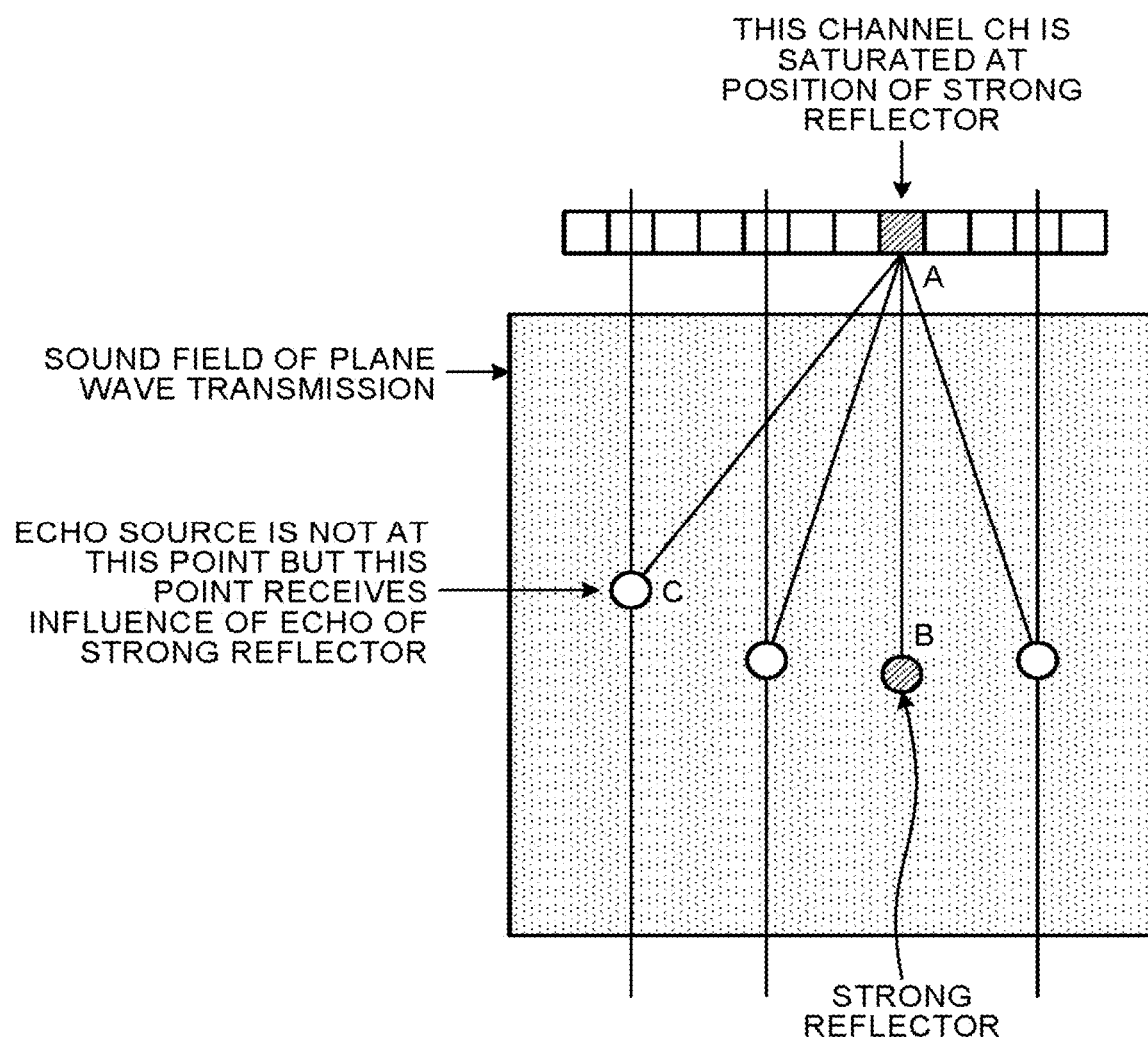
FIG. 4 is a diagram that illustrates an example of a sound field in plane wave transmission.

However, in case of the plane wave transmission illustrated in FIG. 4, focusing is not applied to the transmission, and a beam is narrowed only through reception focusing. For this reason, when a side lobe level of transmission/reception becomes high, a strong reflector is present at a point B as illustrated in FIG. 4, and a signal level of the depth of the point B is saturated in an element A that is disposed just above the point B, a signal level at a position in the distance equal to the distance from the element A to the position B, for example, a point C also increases. Particularly, in many cases, with respect to the echo from the specular reflector, a specific channel CH is saturated. In case of blood flow imaging, since an MTI filter is present, only in the case where the side lobe level is high, imaging is not performed. However, if the specular reflector is rotated according to the moving, the amplitude abruptly changes, and the Doppler band is spread, so that the signal passes through the MTI filter to be displayed as a blood flow signal. Hereinafter, the reason will be described.

FIGS. 5A to 5H are diagrams that illustrate an example of simulation performed in a case where a point reflector (clutter) moves in a direction separating from an ultrasonic beam. FIGS. 5A to 5D illustrate cases where reflected wave signals of all the channels CH are not saturated, and FIGS. 5E to 5H illustrate examples of cases where reflected wave signals of some channels CH are saturated.

Figure 5A:
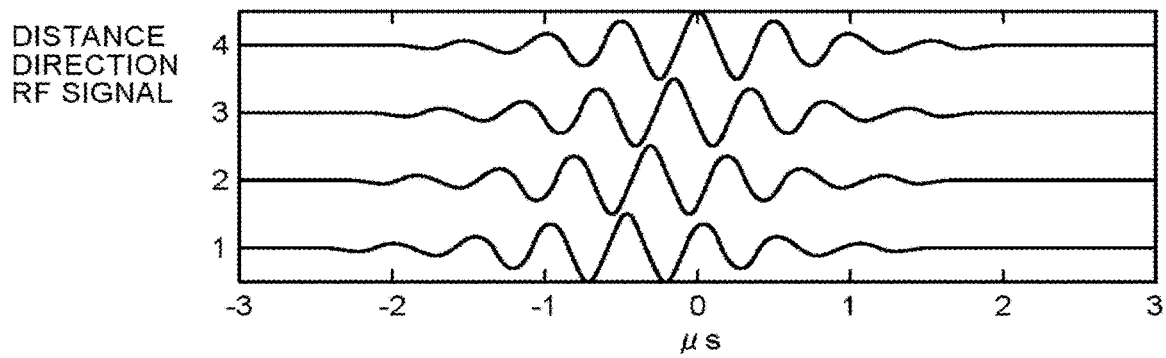
FIG. 5A is a diagram that illustrates an example of RF signals in a distance direction acquired in a case where a point reflector moves in a direction separating from an ultrasonic beam, and reflected wave signals of all channels CH are not saturated.
Figure 5B:
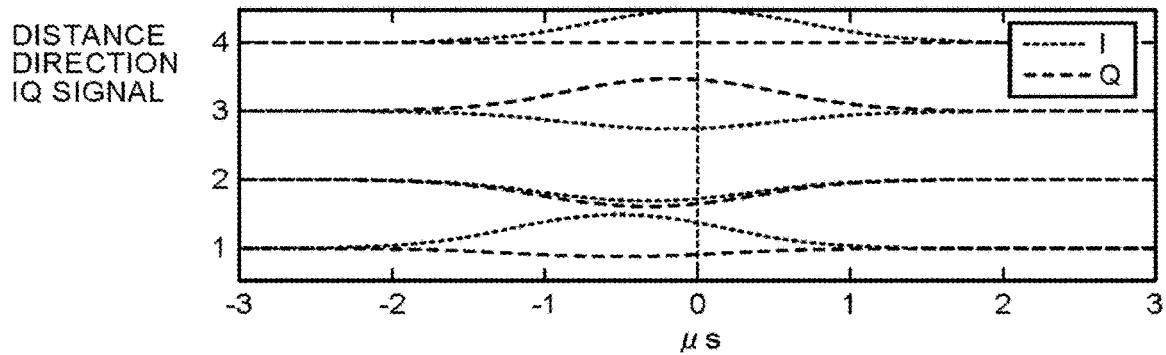
FIG. 5B is a diagram that illustrates an example of IQ signals in a distance direction acquired in a case where a point reflector moves in a direction separating from an ultrasonic beam, and reflected wave signals of all channels CH are not saturated.
Figure 5C:
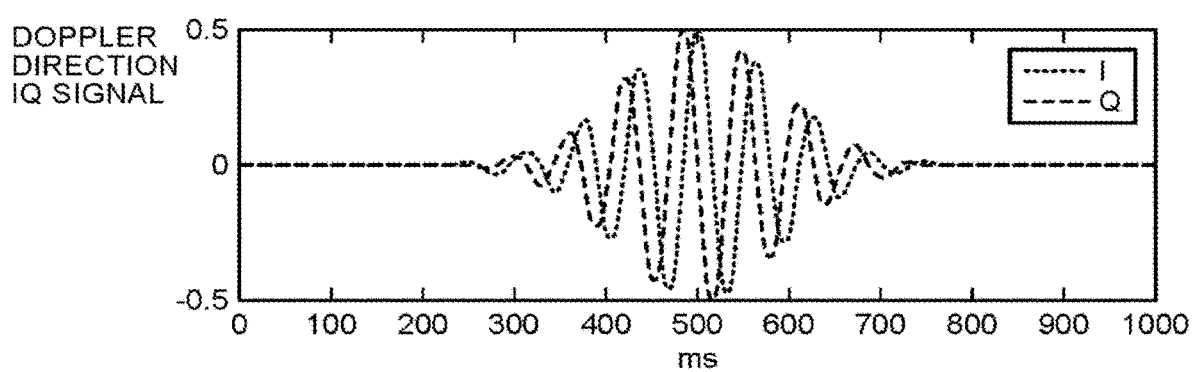
FIG. 5C is a diagram that illustrates an example of IQ signals in a Doppler direction acquired in a case where a point reflector moves in a direction separating from an ultrasonic beam, and reflected wave signals of all channels CH are not saturated.
Figure 5D:
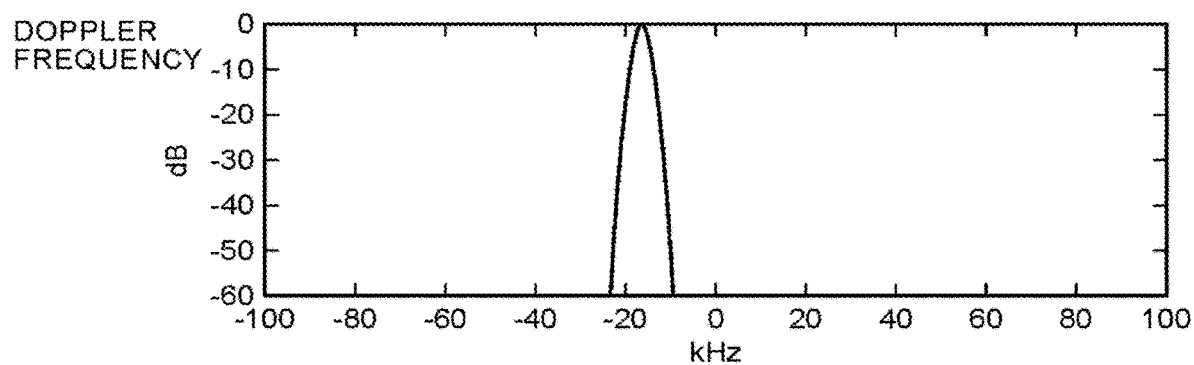
FIG. 5D is a diagram that illustrates an example of a Doppler shift acquired in a case where a point reflector moves in a direction separating from an ultrasonic beam, and reflected wave signals of all channels CH are not saturated.
Figure 5E:
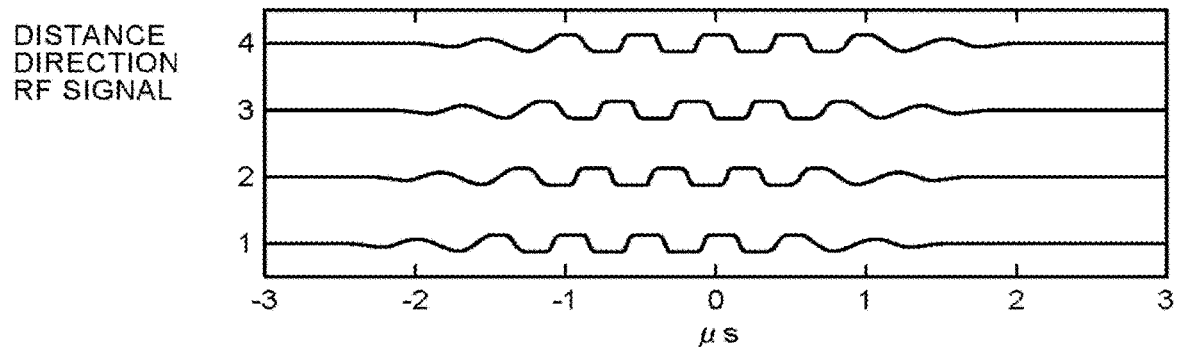
FIG. 5E is a diagram that illustrates an example of RF signals in a distance direction acquired in a case where a point reflector moves in a direction separating from an ultrasonic beam, and reflected wave signals of some channels CH are saturated.

FIGS. 5A and 5E illustrate examples of an RF signal in a distance direction. More specifically, each of FIGS. 5A and 5E illustrates first to fourth reception signals (RF signals) that are received in a case where ultrasonic waves are transmitted four times. Herein, the horizontal axis in each of FIGS. 5A and 5E represents the time, that is, the distance direction, and the vertical axis in each of FIGS. 5A and 5E represents the transmission sequence. For example, "1" in the vertical axis in each of FIGS. 5A and 5E represents a reception signal received in a first transmission period, and "2" in the vertical axis in each of FIGS. 5A and 5E represents a reception signal received in a second transmission period.

Figure 5F:
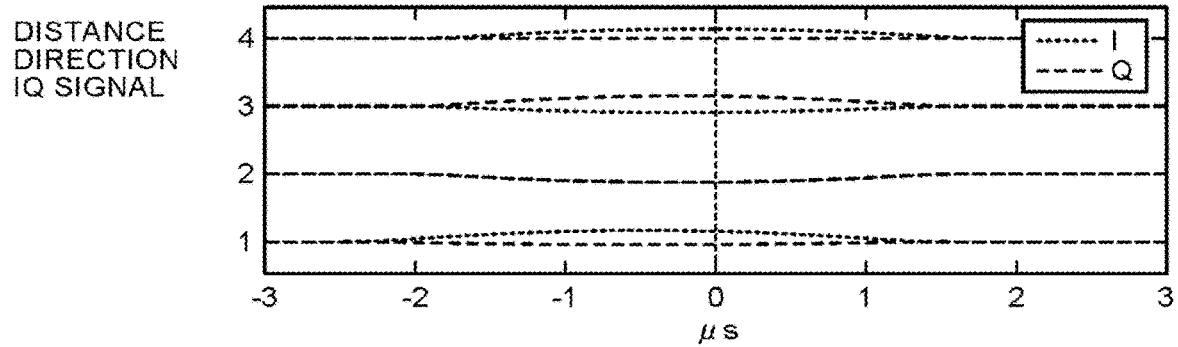
FIG. 5F is a diagram that illustrates an example of IQ signals in a distance direction acquired in a case where a point reflector moves in a direction separating from an ultrasonic beam, and reflected wave signals of some channels CH are saturated.

FIGS. 5B and 5F illustrate examples of I signals and Q signals in the distance direction. Herein, FIGS. 5B and 5F illustrate IQ signals converted from reception signals, similarly to FIGS. 5A and 5E, in a case where an ultrasonic wave is transmitted four times. Herein, the horizontal axis in each of FIGS. 5B and 5F represents the time, that is, the distance direction, and the vertical axis in each of FIGS. 5B and 5F represents the transmission sequence. For example, "1" in the vertical axis in each of FIGS. 5B and 5F represents an IQ signal acquired from a reception signal received in a first transmission period, and "2" in the vertical axis in each of FIGS. 5B and 5F represents an IQ signal acquired from a reception signal received in a second transmission period.

Figure 5G:
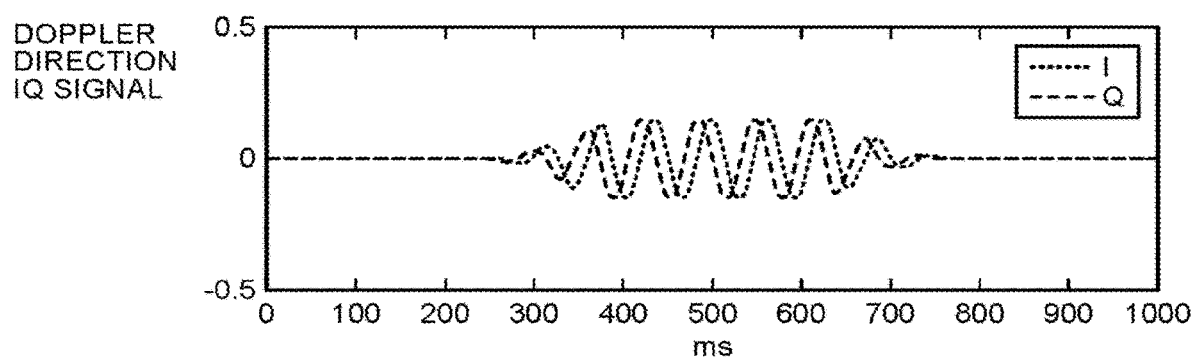
FIG. 5G is a diagram that illustrates an example of IQ signals in a Doppler direction acquired in a case where a point reflector moves in a direction separating from an ultrasonic beam, and reflected wave signals of some channels CH are saturated.

FIGS. 5C and 5G illustrate examples of IQ signals in a Doppler direction that are generated from four IQ signals illustrated in FIGS. 5B and 5F. Herein, the horizontal axis in each of FIGS. 5C and 5G represents the time, that is, the Doppler direction, and the vertical axis in each of FIGS. 5C and 5G represents the amplitude.

Figure 5H:
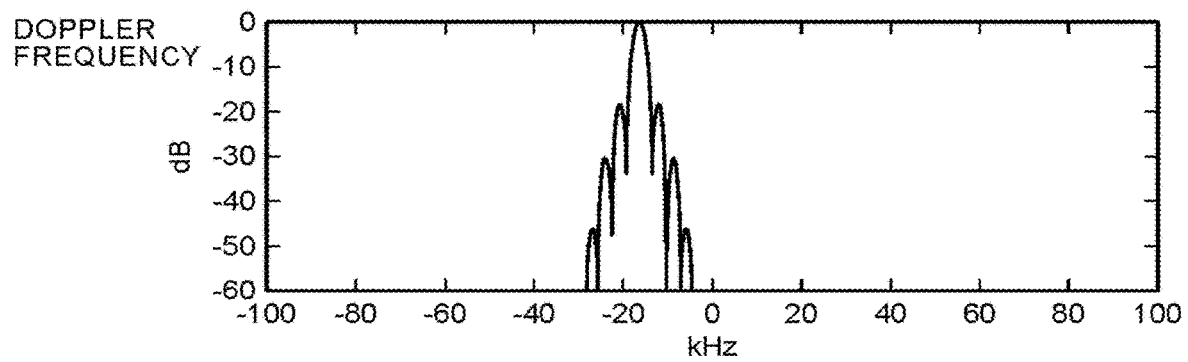
FIG. 5H is a diagram that illustrates an example of a Doppler shift acquired in a case where a point reflector moves in a direction separating from an ultrasonic beam, and reflected wave signals of some channels CH are saturated.

FIGS. 5D and 5H illustrate examples of Doppler shifts calculated using the IQ signals illustrated in FIGS. 5C and 5G. Herein, the horizontal axis in each of FIGS. 5D and 5H represents the Doppler frequency, and the vertical axis in each of FIGS. 5C and 5G represents decibels. In a case where a point reflector (clutter) moves in a direction separating from an ultrasonic beam, as illustrated in FIG. 5D, also in a case where signals are not saturated and, as illustrated in FIG. 5H, also in a case where signals are saturated, there is no large change in a Doppler spectrum. In addition, also when the Doppler spectrum changes to a degree illustrated in FIG. 5H, a clutter can be suppressed using an MTI filter.

Figure 6A:
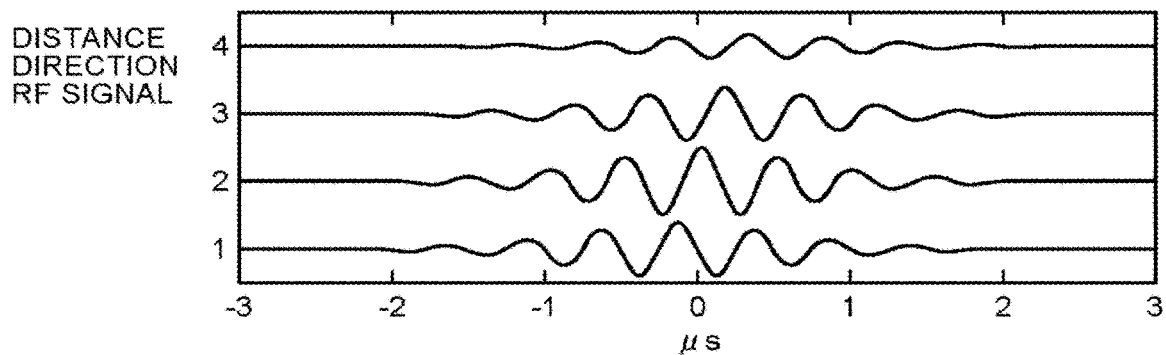
FIG. 6A is a diagram that illustrates an example of RF signals in a distance direction acquired in a case where a point reflector moves to traverse an ultrasonic beam at a high speed, and reflected wave signals of all channels CH are not saturated.
Figure 6B:
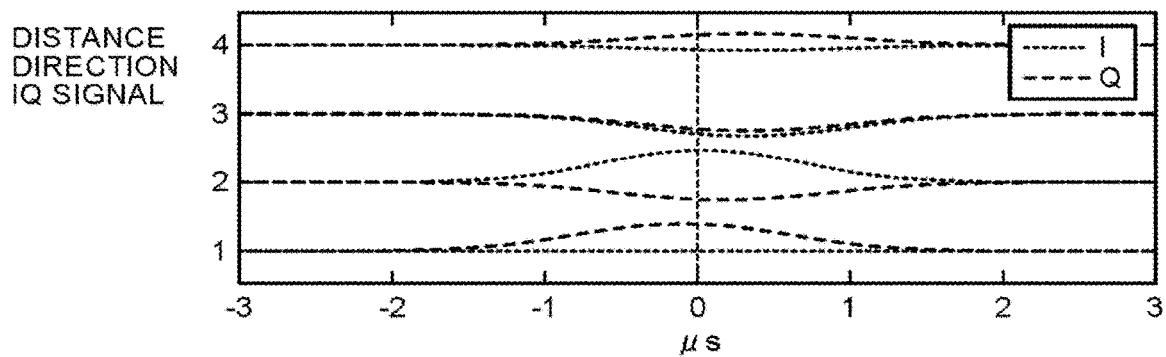
FIG. 6B is a diagram that illustrates an example of IQ signals in a distance direction acquired in a case where a point reflector moves to traverse an ultrasonic beam at a high speed, and reflected wave signals of all channels CH are not saturated.
Figure 6C:
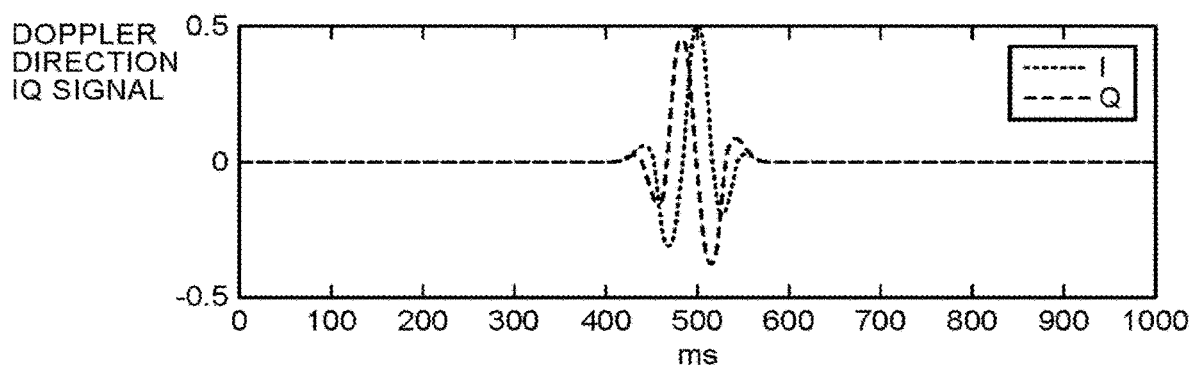
FIG. 6C is a diagram that illustrates an example of IQ signals in a Doppler direction acquired in a case where a point reflector moves to traverse an ultrasonic beam at a high speed, and reflected wave signals of all channels CH are not saturated.
Figure 6D:
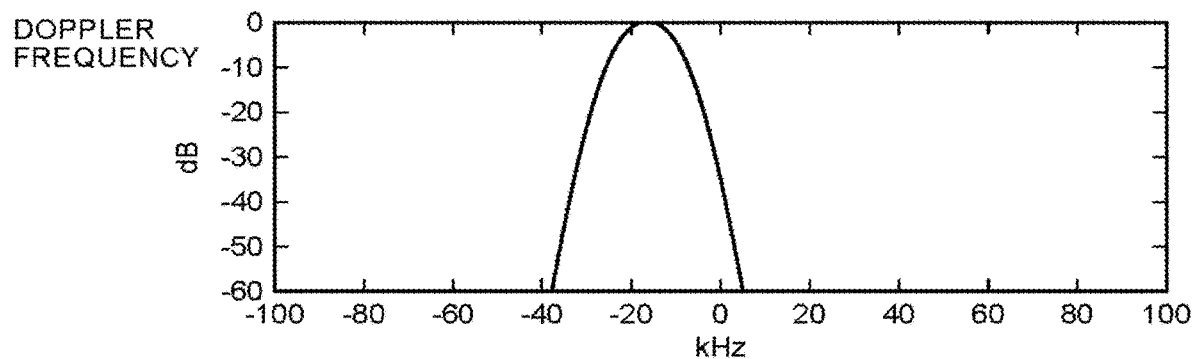
FIG. 6D is a diagram that illustrates an example of a Doppler shift acquired in a case where a point reflector moves to traverse an ultrasonic beam at a high speed, and reflected wave signals of all channels CH are not saturated.
Figure 6E:
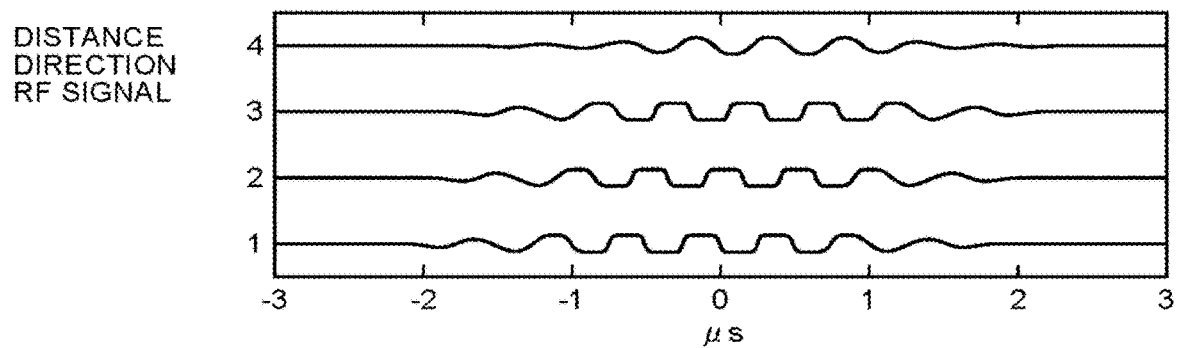
FIG. 6E is a diagram that illustrates an example of RF signals in a distance direction acquired in a case where a point reflector moves to traverse an ultrasonic beam at a high speed, and reflected wave signals of some channels CH are saturated.
Figure 6F:
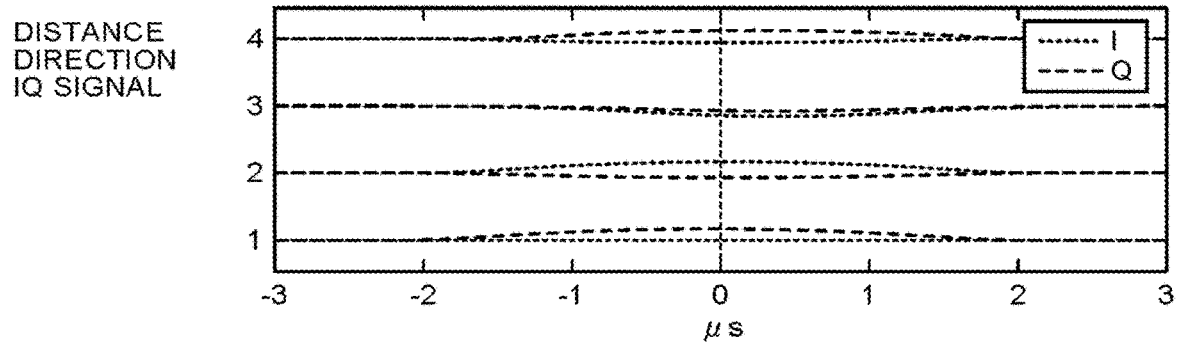
FIG. 6F is a diagram that illustrates an example of IQ signals in a distance direction acquired in a case where a point reflector moves to traverse an ultrasonic beam at a high speed, and reflected wave signals of some channels CH are saturated.
Figure 6G:
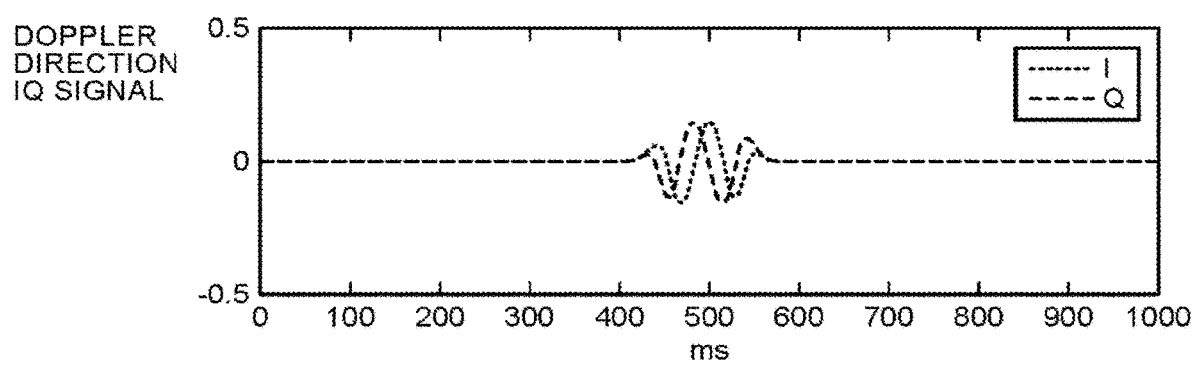
FIG. 6G is a diagram that illustrates an example of IQ signals in a Doppler direction acquired in a case where a point reflector moves to traverse an ultrasonic beam at a high speed, and reflected wave signals of some channels CH are saturated.

FIGS. 6A to 6H are simulation performed in a case where a point reflector moves to traverse an ultrasonic beam at a high speed. FIGS. 6A to 6D illustrate cases where all the channels CH are not saturated, and FIGS. 6E to 6H illustrate examples of cases where some channels CH are saturated. FIGS. 6A and 6E, similarly to FIGS. 5A and 5E, illustrate RF signals in the distance direction. FIGS. 6B and 6F, similarly to FIGS. 5B and 5F, illustrate I signals and Q signals in the distance direction. FIGS. 6C and 6G, similarly to FIGS. 5C and 5G, illustrate IQ signals in the Doppler direction that are generated from four IQ signals.

Figure 6H:
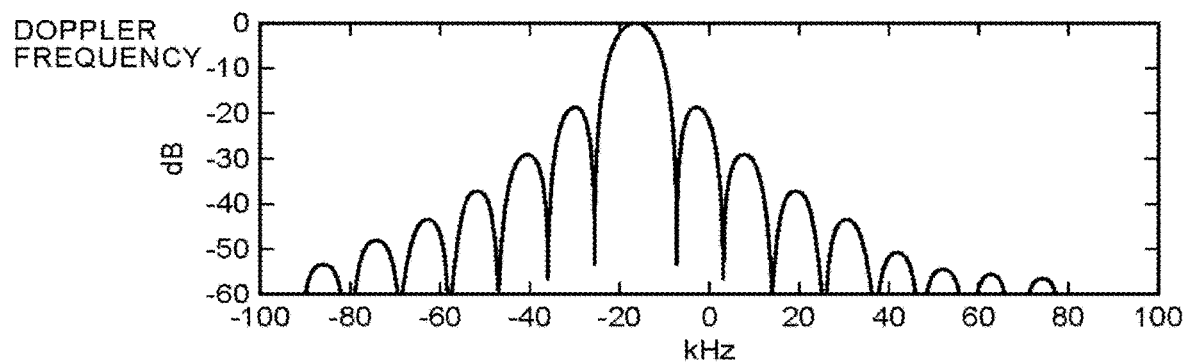
FIG. 6H is a diagram that illustrates an example of a Doppler shift acquired in a case where a point reflector moves to traverse an ultrasonic beam at a high speed, and reflected wave signals of some channels CH are saturated.

FIGS. 6D and 6H, similarly to FIGS. 5D and 5H, illustrate Doppler shifts. Herein, as illustrated in FIG. 6D, in a case where there is no saturation, the Doppler spectrum only expands to some degrees. For this reason, in the case illustrated in FIG. 6D, by setting the cutoff frequency of the MTI filter to be higher than that of the cases illustrated in FIGS. 5D and 5H, a clutter can be suppressed. However, as illustrated in FIG. 6H, in a case where there is saturation, the Doppler spectrum expands up to near a Nyquist frequency, and it is difficult to suppress a clutter using the MTI filter. Differences in the cases in FIGS. 5D and 5H and FIGS. 6D and 6H are that changes in the envelopes are steeper in the cases in FIGS. 6D and 6H than in the cases in FIGS. 5D and 5H. In an actual living body, a tissue hardly moves at a high speed in this way. However, in case of a specular reflector, as an angle changes even in a minute displacement, the envelope abruptly changes. In other words, the artifacts illustrated in FIG. 2 are caused as a signal is specular-reflected from a reception element that is a point on the diaphragm and is specular-reflected or not due to a motion of the diaphragm, and a reception signal acquired by the element is saturated at the time of specular reflection and is not saturated at the time of no specular reflection.

In addition, in the related, the MTI filter process has been performed by the Doppler processing circuitry after the beam forming. FIG. 7 is a diagram that illustrates an example of the configurations of reception circuitry and Doppler processing circuitry according to the conventional technology. As illustrated in FIG. 7, reception circuitry 912 is connected to N transducer elements (Transducer element-1, . . . , Transducer element-N). Herein, each of the transducer elements corresponds to each channel. The transducer element generates an ultrasonic wave based on the transmission signal supplied from transmission circuitry 911. The generated ultrasonic wave is reflected in an in-body tissue of the subject P and is received as a reflected wave signal by a plurality of piezoelectric transducer elements. The transducer element transmits the received reflected wave signal to the reception circuitry 912.

As illustrated in FIG. 7, the reception circuitry 912 includes: amplification circuitry 941-1; an A/D converter 942-1; and quadrature detection circuitry 943-1 as sub circuits used for processing a reflected wave signal received by Transducer element-1. Similarly, the reception circuitry 912 includes: amplification circuitry 941-N; an A/D converter 942-N; and quadrature detection circuitry 943-N as sub circuits used for processing a reflected wave signal received by Transducer element-N. Herein, in a case where the amplification circuitry 941-1 and the amplification circuitry 941-N do not need to be discriminated from each other, the amplification circuitry will be described as amplification circuitry 941. In addition, in a case where the A/D converter 942-1 and the A/D converter 942-N do not need to be discriminated from each other, the A/D converter will be described as an A/D converter 942. In addition, in a case where the quadrature detection circuitry 943-1 and the quadrature detection circuitry 943-N do not need to be discriminated from each other, the quadrature detection circuitry will be described as quadrature detection circuitry 943. Namely, in the reception circuitry 912, the amplification circuitry 941, the A/D converter 942, and the quadrature detection circuitry 943 are disposed for each transducer element (channel). In addition, as described above, the amplification circuitry 941 performs a gain correction process by amplifying a reflected wave signal for each channel. The A/D converter 942 performs A/D conversion of the gain-corrected reflected wave signal. The quadrature detection circuitry 943 converts the reflected wave signal into an in-phase signal (I signal, I: in-phase) and a quadrature signal (Q signal, Q: quadrature phase) of a baseband.

Generation circuitry 944 generates reflected wave data by performing a phasing addition process on the reflected wave signal from each sub circuit. The generation circuitry 944 outputs the generated reflected wave data to Doppler processing circuitry 930.

The Doppler processing circuitry 930 includes: a memory 931; filter processing circuitry 932 (appropriately described as a "filter"); autocorrelation circuitry 933; and calculation circuitry 934. The memory 931 stores the generated reflected wave data generated by the generation circuitry 944. The filter processing circuitry 932 applies an MTI (moving Target Indicator) filter of suppressing a still or slowly-moving signal. The autocorrelation circuitry 933 performs autocorrelation calculation, and the calculation circuitry 934 estimates a speed (V), power (P), and variance (T) of a blood flow signal. Therefore, for example, an ultrasonic diagnostic apparatus according to the conventional technology displays a blood flow image and a B-mode image in a combination manner on a display.

Figure 8:
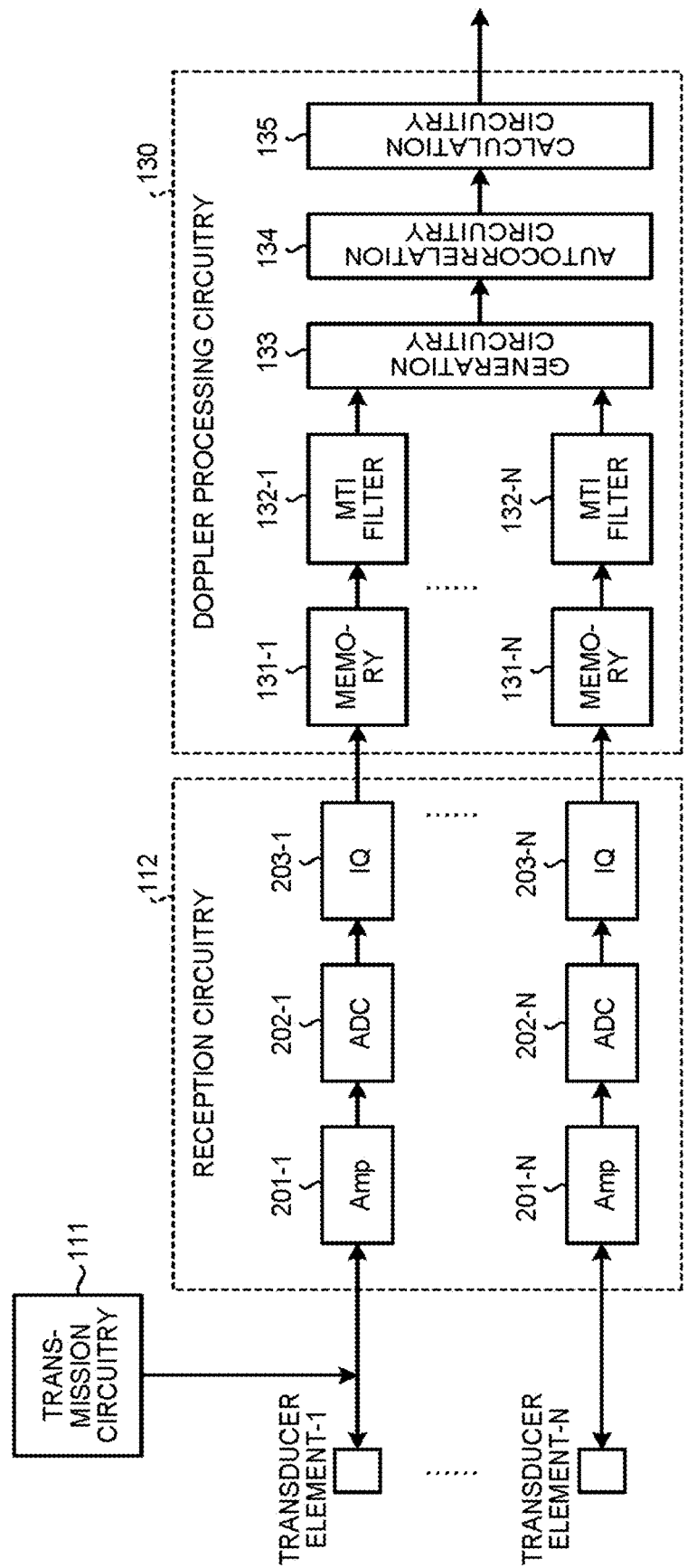
FIG. 8 is a diagram that illustrates an example of the configuration of reception circuitry and Doppler processing circuitry according to the first embodiment.

As illustrated in FIG. 7, while the MTI filter is applied after the beam forming in the conventional example, in the ultrasonic diagnostic apparatus 1 according to the first embodiment, the MTI filter is applied before the beam forming is performed. FIG. 8 is a diagram that illustrates an example of the reception circuitry 112 and the Doppler processing circuitry 130 according to the first embodiment. The transmission circuitry 111 causes the ultrasonic probe 11 to perform ultrasonic wave scanning using a data row between frames as a Doppler data row under the control of the processing circuitry 170 (see Japanese Patent No. 3724846 and Japanese Patent Application Publication No. 2014-42823). For example, the transmission circuitry 111 causes the ultrasonic probe 11 to perform first ultrasonic wave scanning acquiring information relating to a motion of a moving body within a first scanning range and causes the ultrasonic probe 11 to perform ultrasonic wave scanning of each of a plurality of divided ranges acquired by dividing a second scanning range as second ultrasonic wave scanning acquiring information of a shape of a tissue within the second scanning range in a time divisional manner during the first ultrasonic wave scanning under the control of the processing circuitry 170.

As illustrated in FIG. 8, the reception circuitry 112 is connected to N transducer elements (Transducer element-1, . . . , Transducer element-N). Herein, each of the transducer elements corresponds to a channel. In addition, as illustrated in 8, the reception circuitry 112 includes: amplification circuitry 201-1; an A/D converter 202-1; and quadrature detection circuitry 203-1 as sub circuits used for processing a reflected wave signal received by Transducer element-1. Similarly, the reception circuitry 112 includes: amplification circuitry 201-N; an A/D converter 202-N; and quadrature detection circuitry 203-N as sub circuits used for processing a reflected wave signal received by Transducer element-N.

Herein, in a case where the amplification circuitry 201-1 and the amplification circuitry 201-N do not need to be discriminated from each other, the amplification circuitry will be described as amplification circuitry 201. In addition, in a case where the A/D converter 202-1 and the A/D converter 202-N do not need to be discriminated from each other, the A/D converter will be described as an A/D converter 202. In addition, in a case where the quadrature detection circuitry 203-1 and the quadrature detection circuitry 203-N do not need to be discriminated from each other, the quadrature detection circuitry will be described as quadrature detection circuitry 203. Namely, the reception circuitry 112 is provided with the amplification circuitry 201, the A/D converter 202, and the quadrature detection circuitry 203 for each transducer element (channel). In addition, as described above, the amplification circuitry 201 performs a gain correction process by amplifying a reflected wave signal for each channel. The A/D converter 202 performs A/D conversions of the gain-corrected reflected wave signal. The quadrature detection circuitry 203 converts a reflected wave signal into an in-phase signal (I signal, I: In-phase) and a quadrature signal (Q signal, Q: Quadrature-phase) of a baseband. Next, the quadrature detection circuitry 203 transmits the converted I and Q signals to the Doppler processing circuitry 130.

The Doppler processing circuitry 130 includes a memory 131-1 and an MTI filter 132-1 as sub circuits performing a process based on a result of the conversion acquired by the quadrature detection circuitry 203-1 for a reflected wave signal received by Transducer element-1. In addition, the Doppler processing circuitry 130 includes a memory 131-N and an MTI filter 132-N as sub circuits performing a process based on a result of the conversion acquired by the quadrature detection circuitry 203-N for a reflected wave signal received by Transducer element-N. Herein, in a case where the memory 131-1 and the memory 131-N do not need to be discriminated from each other, the memory will be described as a memory 131. In addition, in a case where MTI filter 132-1 and the MTI filter 132-N do not need to be discriminated from each other, the MTI filter will be described as an MTI filter 132. In addition, the MTI filter is also referred to as filter processing circuitry. The Doppler processing circuitry 130 includes: generation circuitry 133; autocorrelation circuitry 134; and calculation circuitry 135.

The memory 131 stores I signals and Q signals converted from reflected wave signals of an ultrasonic wave transmitted a plurality of times in the same scanning line. In addition, the memory 131 is assumed to have a storage capacity capable of storing reflected wave signals of an ultrasonic wave transmitted a plurality of times in the same scanning line.

Figure 9A:
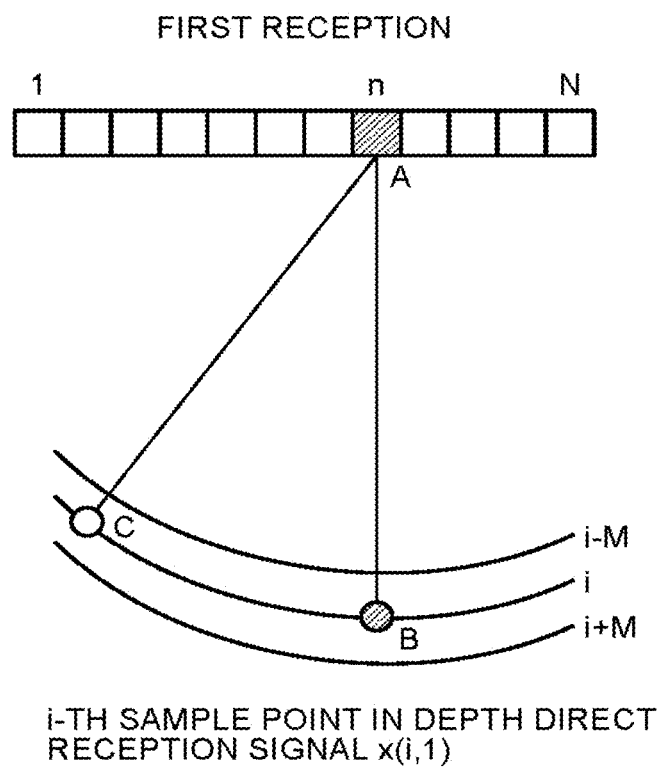
FIG. 9A is a diagram that illustrates the first embodiment.
Figure 9B:
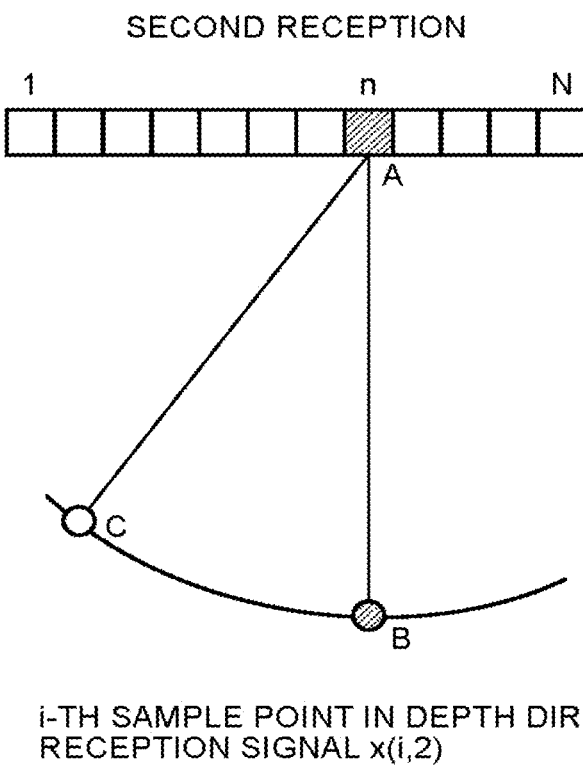
FIG. 9B is a diagram that illustrates the first embodiment.

The MTI filter 132 performs an MTI filtering function. Namely, the MTI filter 132 performs a filter process on reflected wave signals of an ultrasonic wave transmitted a plurality of times in the same scanning line. Herein, the MTI filter 132 performs a filter process of removing a still or minute-moving signal. In other words, the MTI filter 132 performs a filter process of removing a still or minute-moving signal from reflected wave signals of an ultrasonic wave transmitted a plurality of times in the same scanning line. For example, the MTI filter 132 performs a filter process of removing a still or minute-moving signal through a principle component analysis. The MTI filter 132 performs an MTI process on reflected wave signals received from sample points in the same depth direction in the same scanning line. FIGS. 9A to 9C are diagrams that illustrate the first embodiment.

FIG. 9A illustrates a first reception period, FIG. 9B illustrates a second reception period, and FIG. 9C illustrates an L-th reception period. Herein, as illustrated in FIG. 9A, data of each channel CH before the beam forming are received from reflected wave signals located in an equal distance from the transducer element A. More specifically, in FIG. 9A, as the positions located in equal distances transducer element A, (i−M)-th, i-th, and (i+M)-th sample points are illustrated in the depth direction. Hereinafter, a method of calculating the output of the MTI filter at the i-th sample point will be described. In addition, the case where the ultrasonic wave is transmitted L times and L packets are received at the i-th sample point will be described. Herein, L packet data rows of the i-th sample point are represented by a column vector $x_i$ expressed by Mathematical Formula (1).

$$x_i = \begin{pmatrix} x(i, 1) \\ x(i, 2) \\ \vdots \\ x(i, L) \end{pmatrix} \quad (1)$$

Subsequently, the MTI filter 132 calculates a correlation matrix $R_{xx}$ through M spatial ensemble averages before and after the i-th sample point by using the following Mathematical Formula (2). In Mathematical Formula (2), H represents a complex conjugate transpose matrix.

$$R_{xx} = \sum_{m=-M}^{M} x_{i+m} x_{i+m}^H \quad (2)$$

Next, the MTI filter 132 calculates eigen values and eigen vectors of the $R_{xx}$ and generates a matrix V where the eigen vectors are arranged as a column vector in the magnitude order from the left side. Next, the MTI filter 132 calculates an MTI filter matrix W by using the following Mathematical Formula (3).

$$W = V \begin{pmatrix} 0 & & & & \\ & 0 & & & \\ & & \ddots & & \\ & & & 0 & \\ & & & & 1 \end{pmatrix} V^H \quad (3)$$

The matrix in the middle of the right-handed side of Mathematical Formula (3) is a diagonal matrix, the number of zeros arranged from the upper left position is the number of to-be-removed principal components. A value $d_k$ of a k-th diagonal element is determined by a table expressed by the Mathematical Formula (4) according to magnitudes of the eigen values $\lambda_k$ arranged in the magnitude order and ratios with respect to a sum of the eigen values. In the case where $|\lambda_k|$ is a threshold value or more and $|\lambda_k|/\Sigma|\lambda_k|$ is close to 1, the value of the table is set to $d_k=0$, and in the other cases, the value of the table is set to 0.

$$d_k = \text{table}\left(|\lambda_k|, \frac{|\lambda_k|}{\Sigma|\lambda_k|}\right) \quad k = 1 \ldots L \quad (4)$$

Vectors having large eigen values are called principal components, energy of most of all the signals can be approximated by using several principal components. With respect to an echo signal from a tissue and an echo signal from a red blood cell, the echo signal from the tissue is much larger that the echo signal from the red blood cell. Therefore, the principal component may be considered to be the reflected wave signal from the tissue. Accordingly, although a portion of the signal in a packet is saturated, the signal is detected as a principal component. In other words, since the signal is highly likely to be saturated, the signal easily becomes a principal component.

In addition, in a case where the signal is not saturated but there is an abrupt amplitude change according to rotation of the specular reflector, since a signal having a large amplitude due to the specular reflector is included, the signal is recognized as a principal component. Because this occurs before of the beam forming, even in the case of the reflected wave signal of the side lobe of the strong reflector, the signal level of a specific channel CH is very large.

For example, in case of performing the beam forming at the position of the point C illustrated in FIGS. 9A to 9C, it is assumed that a specular reflector does not exist at the point C, and a specular reflector exists at the point B. Herein, if the specular reflector of the point B is not rotated, the signal level from the point C which is received by the transducer element of the channel CH-n existing at the point A is small, and the signal level from the point B which is received by the transducer element of the channel CH-n existing at the point A is large. On the other hand, if the specular reflector of the point B is rotated, the signal level from the point C and the signal level of the point B which are received by the transducer element of the channel CH-n existing at the point A are very large.

For this reason, in the case where the MTI filter is applied after the beam forming, if the specular reflector of the point B is rotated, a clutter signal is displayed at the point C by the side lobe of the point B. However, in the first embodiment, the MTI filter through the principal component analysis is applied on only the reception signal of the channel CH-n before the beam forming. Therefore, since the amplitude at the i-th sample point is very large, the signal is considered to be a principal component, and thus, the reflected wave signal from the specular reflector from the point B is removed by the MTI filter through the principal component analysis. Since the output of the MTI filter at the i-th sample point of the channel CH-n is small, there is no influence of the side lob of the point B on the point C after the beam forming, and thus, a clutter signal is not displayed.

In this manner, after the MTI filter of removing the clutter through the principal component analysis is applied independently for each channel CH, the beam forming is performed, so that the side lobe from the strong reflector can be reduced. At this time, the main lobe from the strong reflector is suppressed simultaneously. In a B-mode image, no display of a tissue image of the strong reflector causes a problem. However, in the blood flow imaging method, since there is no blood vessel in the strong reflector, although a blood flow signal is not displayed, there is no problem.

In a transmission/reception period using a combination of the plane wave transmission and the all-raster parallel simultaneous reception, a case where only a portion of the channels CH is saturated by an echo signal from the specular reflection is considered. In the conventional method of performing adding after the beam forming, due to an abrupt amplitude change according to rotation of the specular reflector, a Doppler component is spread, so that a rapid phase which is incorrectly recognized as a flood flow change occurs, and by adding to other channel CH, the amplitude in the side lobe region is decreased. However, since a phase change remains, the signal cannot be removed by an IIR-type MTI filter or an MTI filter through a principal component analysis. The signal of the channel CH saturated before the beam forming has a large amplitude. Therefore, although there is a rapid phase change due to abrupt amplitude change, the signal can be removed by the MTI filter through the principal component analysis. In this manner, the MTI filter according to the embodiment has such a feature that the MTI filter can remove a signal having a large amplitude independently of whether or not an input signal of the channel CH is saturated.

The generation circuitry 133 performs a beam forming function. Namely, the generation circuitry 133 generated reflected wave data through a phasing addition process using the reflected wave signal of each channel after the filter process performed by the MTI filter 132. The generation circuitry 133 outputs the generated reflected wave data to the autocorrelation circuitry 134.

The autocorrelation circuitry 134 performs autocorrelation calculation by using the reflected wave data generated by the generation circuitry 133, and the calculation circuitry 135 estimates a speed (V), power (P), and variance (T) of a blood flow signal.

As described above, in the ultrasonic diagnostic apparatus 1 according to the first embodiment, after the MTI filter of removing the clutter through the principal component analysis is applied independently for each channel CH, the beam forming is performed, so that the side lobe from the strong reflector can be reduced. As a result, according to the first embodiment, artifacts according to the strong reflector can be reduced. FIG. 10 is a diagram that illustrates an effect of the ultrasonic diagnostic apparatus 1 according to the first embodiment.

FIG. 10 illustrates an example of a case where blood flow information is power-displayed. The left diagram in FIG. 10, similarly to FIG. 2, illustrates a case where artifacts are generated in a circular arc shape including a strong reflector in a case where power display of a blood flow is performed using "plane wave transmission+all-raster parallel simultaneous reception" according to the conventional technology. On the other hand, the right diagram in FIG. 10, illustrates a case where power display of a blood flow is performed using "plane wave transmission+all-raster parallel simultaneous reception" in the ultrasonic diagnostic apparatus 1 according to the first embodiment. As illustrated in the right diagram in FIG. 10, the artifacts having a circular arc shape generated in the left diagram in FIG. 10 disappear. Particularly, in a case where "plane wave transmission+all-raster parallel simultaneous reception" is performed, a remarkable effect is acquired.

In addition, after a process of applying an MTI filter before the beam forming described above, like a conventional case, a process of further applying an MTI filter may be performed after the beam forming. Particularly, by applying an MTI filter according to the principal component analysis described above after beam forming brings further improvement of the elimination of clutter. While an MTI filter using the principal component analysis before beam forming has an effect of decreasing clutter according to a side lobe from a strong reflector, the influence of the main lobe becomes strong after the beam forming, and accordingly, the MTI filter using the principal component analysis has an effect of decreasing clutter according to the main lobe.

The above-described first embodiment may be realized by hardware or by software. For example, in a case where the first embodiment is realized by software, a beam former having an MTI filtering function and a beam forming function is arranged on a rear stage of the reception circuitry and one a front stage of the Doppler processing circuitry. The beam former includes, for example, processing circuitry and a memory and reads a program stored in, storage circuitry 160 to perform the MTI filtering function and the beam forming function.

Second Embodiment

As a second embodiment, a case of performing the following nonlinear process in an MTI filter arranged in each channel CH will be described. In addition, similarly to the first embodiment, it is assumed that transmission circuitry 111 causes an ultrasonic probe 11 to perform ultrasonic wave scanning using a data row between frames as a Doppler data row under the control of processing circuitry 170.

In a case where saturated data is present inside a packet, the data becomes discontinuous. For this reason, in an MTI filter that is a high pass filter (HPF), a signal passes through a discontinuous point, and a tissue-originated signal is incorrectly recognized as a blood flow signal. For example, in a conventional system, there are cases where, as a specular reflector rotates according to a minute motion, a tissue-originated signal passes through the MTI filter. In such cases, a change in the envelope becomes steep, and, even in a case where there is no saturation, as illustrated in FIG. 6D, the Doppler spectrum expands. In a case where there is saturation, as illustrated in FIG. 6H, the Doppler spectrum expands up to near a Nyquist frequency. In such a case, a tissue-originated signal passes through a general MTI filter. As a result, the signal originated from the tissue is displayed as a blood flow signal. In this way, after the beam forming, it cannot be detected whether or not a reflected wave signal is saturated.

Based on such a situation, in the second embodiment, it is determined whether or not a signal is saturated in each channel CH, and in a case where it is determined that a saturated signal is included, as the signal of the channel CH which is determined to be saturated, the signal of the time when it is determined that there is saturation is not used for the beam forming. Herein, in the second embodiment, the case the MTI filtering function of the beam forming function of the Doppler processing circuitry are realized by software will be described. In such a case, a beam former having an MTI filtering function and a beam forming function is arranged on a rear stage of the reception circuitry and on a front stage of the Doppler processing circuitry. The beam former includes, for example, processing circuitry and a memory and reads a program stored in, for example, storage circuitry 160 to perform the MTI filtering function and the beam forming function.

Figure 11:
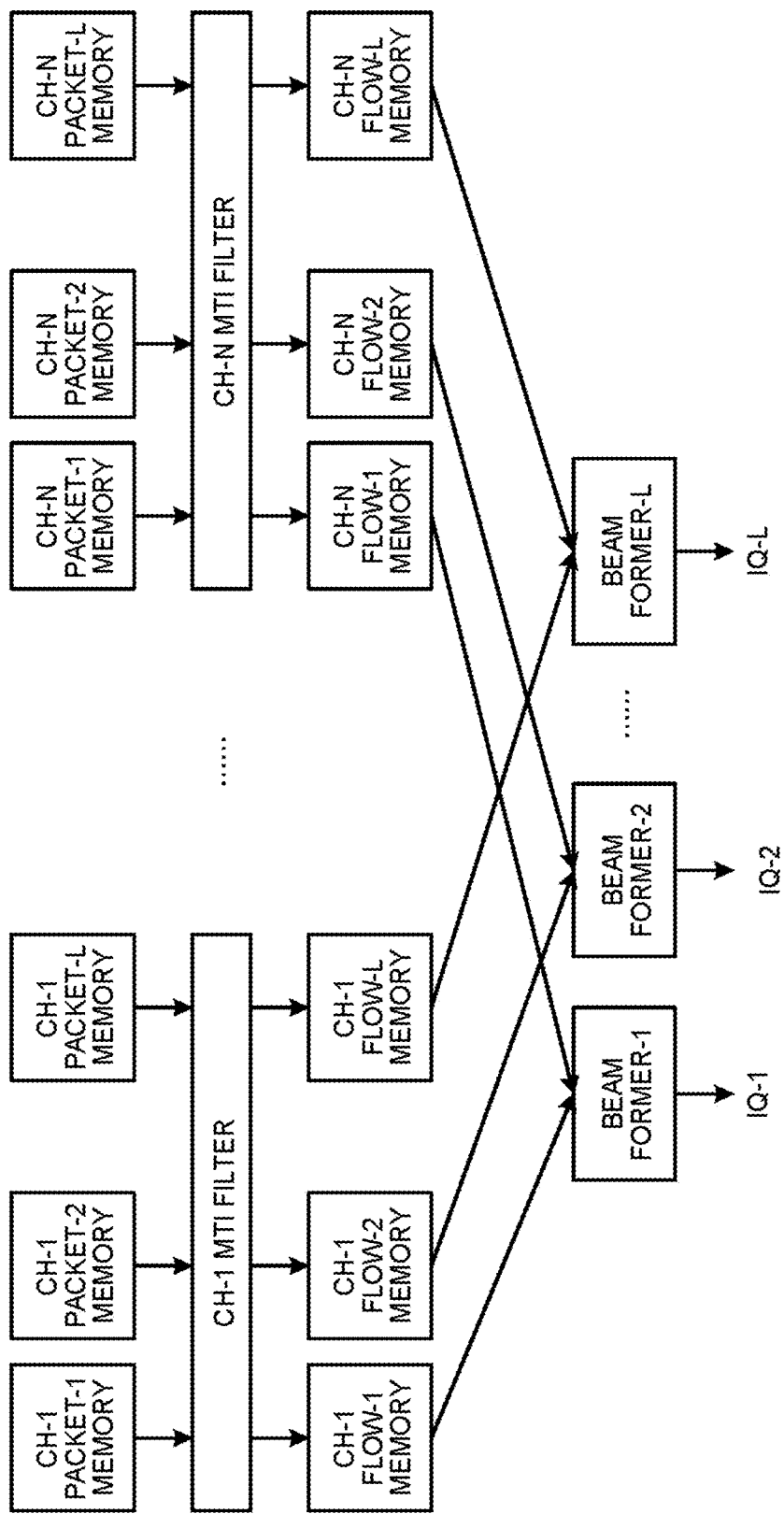
FIG. 11 is a diagram that illustrates a second embodiment.

FIG. 11 is a diagram that illustrates the second embodiment. In FIG. 11, a process of the software is illustrated as a block diagram. It is assumed that there are N reception circuits and a packet size (the number of data of the reflected wave signal which is input to the MTI filter and corresponds to transmission at different time points at the same position) of a color Doppler is L. The MTI filter connected to each channel CH simultaneously reads L data having a size of a packet. In the example illustrated in FIG. 11, a CH-1 MTI filter reads L reflected wave signals of a CH-1 packet-1, a CH-1 packet-2, . . . , and a CH-1 packet-L. Each packet corresponds to each frame. Namely, the CH-1 packet-1 to the CH-N packet-1 correspond to a first frame, and the CH-1 packet-L to the CH-N packet-L correspond to an L-th frame.

The MTI filter of each channel CH performs an MTI filtering function. For example, the MTI filter of each channel CH determines whether or not a reflected wave signal is saturated. Next, the MTI filter of each channel CH sets the output to "0" in a case where there is at least one of saturated data among the data of the L packets. Herein, the MTI filter determines whether or not the data is saturated according to whether or not the output of the A/D converter has a maximum or minimum value. In addition, since there is a possibility that analog circuitry is already saturated near the maximum or minimum value of the output of the A/D converter, instead of the maximum or minimum value, the MTI filter may determine whether or not the data is saturated by using a predetermined threshold value. In a case where there is no saturation in all the data disposed inside the L packets, the MTI filter of each channel CH applies a general MTI filter (for example, a Butterworth infinite impulse response (IIR) filter, a polynomial regression filter, or the like).

Subsequently, the beam former of each channel CH performs the beam forming function to generate reflected wave data through a phasing addition process using the reflected wave signal of each channel after the filter process.

In the method according to the second embodiment, in the case where the signal is saturated, since the signal of the associated channel CH is not used, a tissue is not incorrectly recognized as a blood flow. Since there is generally no blood flow in a tissue boundary which becomes a specular reflector, although a blood flow signal is not output from the portion, there is no problem. In addition, in a case where a reflected wave signal due to a side lobe from a specular reflector and a reflected wave signal of a blood flow exist simultaneously, since the channel CH receiving the reflected wave signal due to the side lobe from the specular reflector is limited to a channel CH perpendicular to the specular reflector, only a portion of the channels CH is saturated. In such a case, since a saturated channel CH is not used and only a non-saturated channel CH is used, the blood flow signal can be extracted by the MTI filter.

In the second embodiment, while the case where the MTI filtering function and the beam forming function are realized by software has been described, the embodiment is not limited thereto. For example, the MTI filtering function and the beam forming function of the Doppler processing circuitry according to the second embodiment may be realized by hardware. In such a case, the reception circuitry is configured in the same manner as that of the reception circuitry illustrated in FIG. 8. In addition, the Doppler processing circuitry is configured in the same manner as that of the Doppler processing circuitry illustrated in FIG. 8 except that the MTI filter and the generation circuitry perform the MTI filtering function and the beam forming function according to the second embodiment.

Third Embodiment

In the first embodiment, as an example of the method of imaging in the same scanning line using a plurality of reflected wave signals, the case of imaging the blood flow information that can be detected from a low speed to a high speed in high frame rate display by the ultrasonic wave scanning using a data row between frames as a Doppler data row was described. However, as another example of the method of imaging in the same scanning line using a plurality of reflected wave signals, there is a pulse inversion method in which two-times transmission is performed with different polarities and a second harmonic is imaged by suppressing a fundamental wave by adding respective reflected wave signals.

Herein, the level of the second harmonic is lower by about −20 dB than that of the fundamental wave. If the reflected wave signal of some channel CH from the strong reflector is saturated, the side lobe level is increased, as illustrated in FIG. 2, due to a motion of a living body or positive or negative nonlinearity, there is a case where a side lobe region becomes an arc-shaped artifact to be displayed with a higher luminance than that of the surrounding. In the case where the signal after addition is saturated, there is a case where a portion of the strong reflector is displayed to be in black. Since such a display as the THI image cause a problem, in actual cases, the gain is allowed to be lowered so as not to cause the problem. However, if the gain is allowed to be lowered, at the time of imaging a minute second harmonic, the sensitivity or the penetration is decreased.

In addition, as one of methods (CHI: Contrast Harmonic Imaging) of imaging a nonlinear signal from an imaging agent, a pulse inversion method is used. In this case, since the ultrasonic wave transmission is performed at such a low sound pressure that the MI value is 0.1 or less, the S/N is originally low. In addition, in order to image the second harmonic from an imaging agent which is lower by about −20 dB than a fundamental wave signal from a tissue, the S/N is further required. In this case, if the gain is raised, the reception signal from the strong reflector is saturated, so that the problem such as THI occurs. Therefore, the gain needs to be set so that such a problem does not occur. Accordingly, there are many cases where sufficient sensitivity or penetration cannot be obtained.

A method of observing a reflected wave signal level of each channel CH in the current frame in order to avoid saturation and changing a gain in the next frame is disclosed. However, in order to avoid saturation from a strong reflector existing in a localized small region, the gain needs to be lowered in a wide region. Furthermore, a decrease in sensitivity in the region where the gain is lowered is inevitable.

For this reason, in the third embodiment, the case of determining whether or not a reflected wave signal received by each channel of the ultrasonic probe 11 is saturated and adding the respective reflected wave signals according to a result of the determination will be described.

The whole configuration of an ultrasonic diagnostic apparatus 1*a* according to the third embodiment is the same as the whole configuration of the ultrasonic diagnostic apparatus 1 according to the first embodiment illustrated in FIG. 1 except for a part of the configuration of reception circuitry, and thus, the description thereof will be omitted.

FIG. 12 is a block diagram that illustrates an example of the configuration of the reception circuitry 112 according to the third embodiment. As illustrated in FIG. 12, the reception circuitry 112 is connected to N transducer elements (Transducer element-1, . . . , Transducer element-N). Herein, each of the transducer elements corresponds to each channel. The output signal of the reception circuitry 112 is connected to the B-mode processing circuitry 120 of FIG. 1.

In addition, in the third embodiment, as illustrated in FIG. 12, for example, the transmission circuitry 111 causes the ultrasonic probe 11 to perform ultrasonic wave scanning having a first transmission ultrasonic wave and a second transmission ultrasonic wave acquired by inverting the phase of the first transmission ultrasonic wave as one set under the control of the processing circuitry 170. For example, the transmission circuitry 111 transmits a transmission pulse in a positive voltage precedence manner in the first period and in a negative voltage precedence manner in the second period at the same raster position.

The reception circuitry 112 includes: amplification circuitry 201-1; an A/D converter 202-1; a line memory 204-1; and PI calculation circuitry 207-1 for processing a reflected wave signal received by Transducer element-1. Similarly, the reception circuitry 112 includes: amplification circuitry 201-N, an A/D converter 202-N; a line memory 204-N; and PI calculation circuitry 207-N for processing a reflected wave signal received by Transducer element-N. Herein, in a case where the amplification circuitry 201-1 and the amplification circuitry 201-N do not need to be discriminated from each other, the amplification circuitry will be described as amplification circuitry 201. In addition, in a case where the A/D converter 202-1 and the A/D converter 202-N do not need to be discriminated from each other, the A/D converter will be described as an A/D converter 202. In addition, in a case where the line memory 204-1 and the line memory 204-N do not need to be discriminated from each other, the line memory will be described as a line memory 204. In addition, in a case where the PI calculation circuitry 207-1 and the PI calculation circuitry 207-N do not need to be discriminated from each other, the PI calculation circuitry will be described as PI calculation circuitry 207.

The amplification circuitry 201 performs a gain correction process by amplifying a reflected wave signal for each channel. For example, the amplification circuitry 201 performs a gain correction process by amplifying a reflected wave signal (first reflected wave signal) of the first transmission ultrasonic wave and a reflected wave signal (second reflected wave signal) of the second transmission ultrasonic wave. The A/D converter 202 performs A/D conversion of the gain-corrected reflected wave signal. For example, the A/D converter 202 performs A/D conversion of the gain-corrected first reflected wave signal and the gain-corrected second reflected wave signal. The A/D converter 202 transmits the first reflected wave signal of which the A/D conversion has been performed and second reflected wave signal of which the A/D conversion has been performed to the line memory 204. The line memory 204 stores first data which is A/D-converted after the amplification by the amplification circuitry 201 for each channel CH. In other words, the line memory 204 stores the first reflected wave signal of which the A/D conversion has been performed and the second reflected wave signal of which the A/D conversion has been performed.

The PI calculation circuitry 207 adds the reflected wave signal of the first transmission ultrasonic wave and the reflected wave signal of the second transmission ultrasonic wave in the same scanning line and performs a filter process of extracting the reflected wave signal of the harmonic component. For example, at the time of performing the second reception, the PI calculation circuitry 207 adds the first signal and the second signal at the same position.

Herein, the PI calculation circuitry 207 determines whether or not at least one of a reflected wave signal of the first transmission ultrasonic wave and a reflected wave signal of the second transmission ultrasonic wave, which have been received by each channel of the ultrasonic probe 11. In the case where the PI calculation circuitry 207 determines that the signal is saturated, the PI calculation circuitry outputs an output signal where a value of the reflected wave signal of a harmonic component is "0". On the other hand, in the case where the PI calculation circuitry 207 determines that the signal is not saturated, the PI calculation circuitry outputs, as an output signal, the reflected wave signal of the harmonic component obtained by adding the reflected wave signal of the first transmission ultrasonic wave and the reflected wave signal of second transmission ultrasonic wave and performing extraction. Herein, the PI calculation circuitry 207 determines whether or not the signal is saturated according to whether or not the output of the A/D converter 202 has a maximum or minimum value. Since there is a possibility that analog circuitry is already saturated near the maximum or minimum value, instead of the maximum or minimum value, comparison with a predetermined threshold value may be performed. Generation circuitry 206 generates reflected wave data by using an output signal output by the PI calculation circuitry 207.

In addition, the B-mode processing circuitry 120 generates B mode data from the reflected wave data generated by the generation circuitry 206. The B-mode processing circuitry 120 outputs the generated B mode data to the image generating circuitry 140. In this way, the image generating circuitry 140 generates an ultrasonic wave image by using signals acquired by extracting the harmonic component from the reflected wave data generated by the generation circuitry 204 as a result of the ultrasonic wave scanning.

The ultrasonic diagnostic apparatus 1a according to the third embodiment can raise the gain to be higher than that of a conventional case in a case where a nonlinear signal is acquired from a tissue or an imaging agent without using the blood flow imaging method. For this reason, the S/N ratio is improved, and the sensitivity and the penetration can be improved. In addition, in most cases, since an echo source having a strong reflection intensity is specular reflection, the angle dependency is strong. For this reason, in small cases, all the channels CH are saturated. Therefore, although the output of the saturated channel CH is set to "0", since a signal can be obtained from other channel CH, the tissue image is correctly displayed.

In addition, in the third embodiment, while the example of performing two times of transmission with polarities being reversed has been described, the same process is available for a case of performing three or more of transmission with phases being different.

In addition, after the PI addition process is performed before the above-described beam forming, similarly to the related art, after the beam forming, a PI addition process may be further performed.

Other Embodiment

The embodiment is not limited to the embodiments described above.

The first embodiment to the third embodiment described above may be combined and used.

In the first embodiment to the third embodiment described above, the process performed by the ultrasonic diagnostic apparatus may be performed by an apparatus other than the ultrasonic diagnostic apparatus. For example, a signal of each channel CH before beam forming is stored in the storage circuitry 160 from the reception circuitry 112 through a bus. Then, the apparatus other than the ultrasonic diagnostic apparatus, for example, may display an image by reading a signal of each channel CH before beam forming after the stop of ultrasonic wave scanning, outputting data using the method described in the first embodiment and the second embodiment described above, and performing B-mode processing and color Doppler processing. For example, the signal processing unit includes filter processing circuitry and generation circuitry. The filter processing circuitry performs a filter process on reflected wave signals of an ultrasonic wave transmitted a plurality of times in the same scanning line. The generation circuitry generates reflected wave data through a phasing addition process using the reflected wave signal of each channel after the filter process performed by the filter processing circuitry.

In the description of the embodiments described above, each constituent element of each apparatus illustrated in the drawing is functional and conceptual, and it is not necessary to physically configure each apparatus as illustrated in the drawing. In other words, a specific form of separation/integration of each apparatus is not limited to that illustrated in the drawing, and the whole or a part of each apparatus may be functionally or physically distributed/integrated in an arbitrary unit in accordance with various loads, the use status, and the like. In addition, the entirety or an arbitrary part of each processing function performed in each apparatus may be realized by a CPU and a program that is interpreted and executed by the CPU or may be realized by hardware using a wired logic.

In addition, the control method described in the embodiments described above may be realized by executing a control program prepared in advance using a computer such as a personal computer or a workstation. This control program may be distributed through a network such as the Internet. In addition, this control program may be recorded on a computer-readable recording medium such as a hard disk, a flexible disk (FD), a CD-ROM, an MO, or a DVD and can be executed by being read by a computer from the recording medium.

According to at least one of the embodiments described above, artifacts according to a strong reflector can be decreased.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
control circuitry configured to cause an ultrasonic probe to perform ultrasonic wave scanning having a first transmission ultrasonic wave and a second transmission ultrasonic wave produced by inverting a phase of the first transmission ultrasonic wave;
filter processing circuitry configured to perform a filter process of adding a reflected wave signal of the first transmission ultrasonic wave and a reflected wave signal of the second transmission ultrasonic wave in a same scanning line in order to extract a reflected wave signal of a harmonic component, the reflected wave signals each corresponding to a channel, producing filtered signals; and
generation circuitry configured to generate reflected wave data through a phasing addition process of the filtered signals, wherein
the filter processing circuitry determines whether or not at least one of the reflected wave signal of the first transmission ultrasonic wave and the reflected wave signal of the second transmission ultrasonic wave received by each channel of the ultrasonic probe is saturated, in a case where it is determined that at least one is saturated, the filter processing circuitry outputs a value of 0 for the reflected wave signal of the harmonic component as an output signal, and in a case where it is not determined that at least one is saturated, the filter processing circuitry outputs the reflected wave signal of the harmonic component obtained by adding the reflected wave signal of the first transmission ultrasonic wave and the reflected wave signal of the second transmission ultrasonic wave and performing the extracting as an output signal, and
the generation circuitry generates the reflected wave data by using the output signal output by the filter processing circuitry.

2. The ultrasonic diagnostic apparatus according to claim 1, further comprising control circuitry configured to cause an ultrasonic probe to perform ultrasonic wave scanning which transmits a plane wave.

3. The ultrasonic diagnostic apparatus according to claim 2, wherein the control circuitry causes the ultrasonic probe to perform ultrasonic wave scanning which receives the reflected wave signals through a plurality of scanning lines.

4. A signal processing apparatus, comprising:
filter processing circuitry configured to, in ultrasonic wave scanning being performed by an ultrasonic probe and having a first transmission ultrasonic wave and a second transmission ultrasonic wave produced by inverting a phase of the first transmission ultrasonic wave, perform a filter process of adding a reflected wave signal of the first transmission ultrasonic wave and a reflected wave signal of the second transmission ultrasonic wave in a same scanning line in order to extract a reflected wave signal of a harmonic component, the reflected wave signals each corresponding to a channel, producing filtered signals; and
generation circuitry configured to generate reflected wave data through a phasing addition process of the filtered signals, wherein
the filter processing circuitry determines whether or not at least one of the reflected wave signal of the first transmission ultrasonic wave and the reflected wave signal of the second transmission ultrasonic wave received by each channel of the ultrasonic probe is saturated, in a case where it is determined that at least one is saturated, the filter processing circuitry outputs a value of 0 for the reflected wave signal of the harmonic component as an output signal, and in a case where it is not determined that at least one is saturated, the filter processing circuitry outputs the reflected wave signal of the harmonic component obtained by adding the reflected wave signal of the first transmission ultrasonic wave and the reflected wave signal of the second transmission ultrasonic wave and performing the extracting as an output signal, and
the generation circuitry generates the reflected wave data by using the output signal output by the filter processing circuitry.

5. The signal processing apparatus according to claim 4, comprising:
the filter processing circuitry configured to determine whether at least one of the reflected wave signals is saturated wherein, in a case where one of the reflected wave signals is determined to be saturated, the filter processing circuitry excludes the one reflected wave signal from the produced filtered signals.

* * * * *